(12) United States Patent
Jeong et al.

(10) Patent No.: US 7,087,244 B2
(45) Date of Patent: Aug. 8, 2006

(54) THERMOGELLING OLIGOPEPTIDE POLYMERS

(75) Inventors: Byeongmoon Jeong, Seoul (KR); Anna Gutowska, Richland, WA (US)

(73) Assignee: Battelle Memorial Institute, Richland, WA (US)

(*) Notice: Subject to any disclaimer, the term of this patent is extended or adjusted under 35 U.S.C. 154(b) by 386 days.

(21) Appl. No.: 10/124,614

(22) Filed: Apr. 16, 2002

(65) Prior Publication Data
US 2004/0077780 A1    Apr. 22, 2004

Related U.S. Application Data

(63) Continuation-in-part of application No. 09/833,460, filed on Apr. 11, 2001, now Pat. No. 6,841,617.

(60) Provisional application No. 60/236,926, filed on Sep. 28, 2000.

(51) Int. Cl.
*A61K 9/00* (2006.01)
*C08L 51/00* (2006.01)
*C08L 53/00* (2006.01)

(52) U.S. Cl. .................. 424/486; 424/499; 523/200; 524/504; 524/505; 524/845; 528/271

(58) Field of Classification Search ............... 524/845, 524/504, 505; 523/200; 528/271; 424/486, 424/499
See application file for complete search history.

(56) References Cited

U.S. PATENT DOCUMENTS

| | | | |
|---|---|---|---|
| 4,179,337 A * | 12/1979 | Davis et al. ............. 435/181 |
| 4,438,253 A | 3/1984 | Casey et al. |
| 4,526,938 A | 7/1985 | Churchill et al. |
| 4,904,584 A * | 2/1990 | Shaw ..................... 435/69.4 |
| 4,942,035 A * | 7/1990 | Churchill et al. ........... 514/15 |
| 4,946,686 A | 8/1990 | McClelland et al. |
| 5,213,580 A | 5/1993 | Slepian et al. |
| 5,278,201 A | 1/1994 | Dunn et al. |
| 5,449,513 A | 9/1995 | Yokoyama et al. |
| 5,462,990 A | 10/1995 | Hubbell et al. |
| 5,575,815 A | 11/1996 | Slepian et al. |
| 5,634,946 A | 6/1997 | Slepian |
| 5,646,131 A | 7/1997 | Badwan et al. |
| 5,662,609 A | 9/1997 | Slepian |
| 5,674,287 A | 10/1997 | Slepian et al. |
| 5,702,717 A | 12/1997 | Cha et al. |
| 5,749,915 A | 5/1998 | Slepian |
| 5,749,922 A | 5/1998 | Slepian et al. |
| 5,843,156 A | 12/1998 | Slepian et al. |
| 5,858,746 A | 1/1999 | Hubbell et al. |
| 6,004,573 A | 12/1999 | Rathi et al. |
| 6,007,845 A | 12/1999 | Domb et al. |
| 6,060,582 A | 5/2000 | Hubbell et al. |
| 6,083,486 A * | 7/2000 | Weissleder et al. .......... 424/9.6 |
| 6,083,524 A | 7/2000 | Sawhney et al. |
| 6,117,949 A | 9/2000 | Rathi et al. |
| 6,290,729 B1 | 9/2001 | Slepian et al. |
| 6,352,682 B1 | 3/2002 | Leavitt et al. |
| 6,443,941 B1 | 9/2002 | Slepian et al. |
| 2001/0034050 A1 | 10/2001 | Chilkoti |
| 2002/0032309 A1 | 3/2002 | Deming et al. |
| 2002/0131935 A1 | 9/2002 | Fisher et al. |
| 2002/0168319 A1 | 11/2002 | Filler et al. |
| 2004/0228794 A1 * | 11/2004 | Weller et al. .............. 424/1.11 |

FOREIGN PATENT DOCUMENTS

| | | |
|---|---|---|
| WO | WO 95/00162 | 1/1995 |
| WO | WO 9603112 | 2/1996 |
| WO | WO 98/55147 | 12/1998 |
| WO | WO 99/07343 | 2/1999 |
| WO | WO 99/18142 | 4/1999 |
| WO | WO99/55386 | 11/1999 |
| WO | WO 00/21574 | 4/2000 |
| WO | WO 00/56774 | 9/2000 |
| WO | WO 01/67104 | 9/2001 |
| WO | WO 02/26215 | 4/2002 |
| WO | WO03/087196 | 10/2003 |

OTHER PUBLICATIONS

Deming, Timothy J., "Facile synthesis of block copolypeptides of defined architecture," *Nature*, vol. 390, pp. 386-390 (Nov. 1997).

Behravesh, E. et al., "Synthesis and Characterization of Triblock Copolyers of Methoxy Poly(ethylene glycol) and propylene fumarate),"pp. A-F (2001).

Alexandridis, P. et al., "Micellization of Poly(ethykene oxide)-Poly(propylene oxide)-Poly(ethylene oxide) Triblock Copolymers in Aqueous Solutions. Thermodynamics of Copolymer Association," pp. 2414-2425 (1994).

(Continued)

*Primary Examiner*—Tae H. Yoon
(74) *Attorney, Agent, or Firm*—Klarquist Sparkman, LLP

(57) ABSTRACT

Disclosed is a thermogelling biodegradable aqueous polymer solution useful in providing a bioactive agent delivery system. A thermogelling biodegradable aqueous polymer solution may comprise a biocompatible block and a biodegradable polypeptide block, where the blocks are linked to form a polymer of a general structure comprising the formula of $C_nD_m$, wherein n is equal to or greater than 1, m is equal to or greater than 1, C is a biodegradable polypeptide block, and D is a biocompatible soluble polymer having a chain length such that if D is not biodegradable, D may be eliminated through a glomeruli filtration system.

25 Claims, 15 Drawing Sheets

OTHER PUBLICATIONS

Bellare, JR. et al., "Controlled Enviroment Vitrification System: An Improved Sample Preparation Technique," pp. 87-111 (1988).

Betre, H. et al., "Injectable Elastin-Like Polypeptide for Cartilage Repair," 47th Annual Meeting, Orthopaedic Research Society, p. 601 (Feb. 25-28, 2001).

Brown, W. et al., "Micelle and Gel Formation in a Poly(ethylene oxide)/Poly(propylene oxide)/Poly(ethylene oxide) Triblock Copolymer in Water Solution. Dynamic and Static Light Scattering and Oscillatory Sheer Measurements," pp. 1850-1858 (1991).

Cau, Fl et al., "H NMR Relaxation Studies of the Micellization of a Poly(ethylene oxide)-Poly(propylene oxide)-Poly(propylene oxide)-Poly(ethylene oxide) Triblock Copolymer in Aqueous Solution," pp. 170-178 (1996).

Chen, G. et al., "Graft Copolymers that Exhibit Temperature-Induced Phase Transitions Over a Wide Range of pH," pp. 49-52 (1995).

Deng, Y. et al., "Thermodynamics of Micellisation and gelation of Oxyethylene/Oxypropylene Diblock Copolymers in Aqueous Solution Studied by Light Scattering and Differential Scanning Calorimetry," pp. 1441-1446 (1992).

Discher, BM. et al., "Polymersomes: Tough Vesicles Made From Diblock Copolymers," pp. 1-9 (1999).

Feil, H. et al., "Effects of Comonomer Hydrophilicity and Ionization on the Lower Critical Solution Temperature of N-Isopropylacrylamide Copolymers," pp. 2496-2500 (1993).

Gutowska, A. et al., "Injectable Gels for Tissue Engineering," pp. 1-26 (2000).

Hill-West, JL. et al., "Inhibition of Thrombosis and Intimal Thickening by in situ Photopolymerization of Thin Hydrogel Barriers," pp. 5967-5671 (1994).

Israelachvili, JN., "Intermolecular and Surface Forces," pp. 102-106 & 207-208 (1985).

Jeong, B. et al., "Biodegradable Block Copolymers as Injectable Drug-Delivery Systems," pp. 860-862 (1997).

Jeong, B. et al., "Diodegradable Thermoreversible Gelling Polymer with a Maximum Modulus at Body Temperature," pp. 1-13 (2000).

Jeong, B. et al., "Biodegradable Thermosensitive Micelles of PEG-PLGA-PEG Triblock Copolymers," pp. 185-193 (1999).

Jeong, B. et al., "Drug Release from Biodegradable Injectable Thermosensitive Hydrogel of PEG-PLGA-PEG Triblock Copolymers," pp. 155-163 (2000).

Jeong, B. et al., "In situ Gelation of PEG-PLGA-PEG Triblock Copolymer Aqueous Solutions and Degradation Thereof," pp. 171-177 (2000).

Jeong, B. et al., "New Biodegradable Polymers for Injectable Drug Delivery Systems," pp. 109-114 (1999).

Jeong, B. et al., "Reverse Thermogelling Biodegradable Polymers: PEG-g-PLGA," pp. 1-6.

Jeong, B. et al., "Thermogelling Biodegradable Polymers with Hydrophilic Backbones: PEG-g-PLGA," pp. A-F (2000).

Jeong, B. et al., "Thermoreversible Gelation of PEG-PLGA-PEG Triblock Copolymer Aqueous Solutions," pp. 7064-7069 (1999).

Jeong, B. et al., "Thermoreversible Gelatin of Poly(Ethylene Oxide) Biodegradable Polyester Block Copolymers," pp. 751-760 (1998).

Jhon, MS. et al., "Water and Hydrogels," pp. 509-522 (1973).

Johnston, TP. et al., "Sustained Delivery of Interleukin-2 From a Polymer 407 Gel Matrix Following Intraperitoneal Injection of Mice," pp. 425-434 (1992).

Malmsten, M. et al., "Self-Assembly in Aqueous Block Copolymer Solutions," pp. 5440-5445 (1992).

Meyer, DE. et al., "Drug Targeting Using Thermally Responsive Polymers and Local Hyperthermia," *Journal of Controlled Release*, vol. 71, pp. 213-224 (2001).

Moiseev, L., "Temperature-Dependent Properties of Elastin-like Polypeptides (ELP)," http://www.bu.edu/mcbb/calendar_of_events/abstracts/moiseev_abstract.htm, (Jan. 21, 2000).

Nath, N. et al., "Interfacial Phase Transition of an Environmentally Responsive Elastin Biopolymer Adsorbed on Functionalized Gold Nanoparticles Studied by Colloidal Surface Plasmon Resonance," *J. Am. Chem. Soc.*, vol. 123, pp. 8197-8202 (2001).

Odian, G., "Principles of Polymerization," pp. 512-515 (1981).

Raucher, D. et al., "Enhanced Uptake of a Thermally Responsive Polypeptide by Tumor Cells in Responsive to its Hyperthermia-mediated Phase Transition," *Cancer Research*, vol. 61, pp. 7163-7170 (Oct. 1, 2001).

Rosiak, JM. et al., "Hydrogels for Biomedical.Purposes," pp. 335-339 (1995).

Stile, RA. et al., "Synthesis and Characterization of Injectable Poly(N-isopropylacrylamide)-Based Hydrogels that Support Tissue Formation *in Vitro*," pp. 7370-7379 (1999).

Tanodekaew, S. et al., "Gelation of Aqueous Solutions of Diblock Copolymers of Ethylene Oxide and $_{D,L}$-Lactide," pp. 3385-3395 (1997).

Thomas, JL. et al., "Tuning the Response of a pH-Sensitive Membrane Switch," pp. 2949-2950 (1995).

Wanka, G. et al., "The Aggregation Behavior of Poly-(oxyethylene)-Poly-(oxypropylene)-Poly-(oxyethylene)-Block-Copolymers in Aqueous Solution," pp. 101-117 (1990).

Wout, ZGM, et al., "Poloxamer 407-Mediated Changes in Plasma Cholesterol and Triglycerides Following Intraperitoneal Injection to Rats," pp. 192-200 (1992).

Yang, Z. et al., "Effects of Block Structure on the Micellization and Gelation of Aqueous Solutions of Copolymers of Ethylene Oxide and Butylene Oxide," pp. 2371-2379 (1994).

Yu, GE. et al., "Micellisation and Gelation of Triblock Copoly(oxyethylene/oxypropylene/oxyethylene), F127," pp. 2537-2544 (1992).

Zhou, Z. et al., "Light-Scattering Study on the Association Behavior of Triblock Polymers of Ethylene Oxide and Propylene Oxide in Aqueous Solution," pp. 171-180 (1988).

Won, YY. et al., "Giant Wormlike Rubber Micelles," pp. 960-963 (1999).

"Genetically Engineered Biomolecules May Help Cancer Treatment Delivery," http://www.dukenews.duke.edu/Daily00-01/chil.htm, (Mar. 9, 2001).

Chilkoti, A. et al., "A genetically Engineered Polypeptide Carrier for Thermal Targeting of Therapeutics."

R. T. Piervincenzi Article—Research Interests: Exploring Protein Engineering to Develop Novel Molecular Tools for Improving Application in the Fields of Drug Delivery and Biosensor Development.

Kawashita et al., "Preparation of Ceramic Microspheres for in situ Radiotherapy of Deep-Seated Cancer," Biomaterials, 24(17):2955-2963 (2003).

PCT International Search Report (PCT/US2005/005158), 5pp. (Jan. 18, 2006).

* cited by examiner

THERMOGELLING OLIGOPEPTIDE POLYMERS

CROSS REFERENCE TO RELATED APPLICATIONS

This application is a continuation-in-part of patent application Ser. No. 09/833,460, filed Apr. 11, 2001 now U.S. Pat. No. 6,841,617, which application claims the benefit under 35 U.S.C. §119(e) of provisional Patent Application No. 60/236,926, filed Sep. 28, 2000.

FIELD OF THE INVENTION

The disclosure relates to a thermogelling biodegradable aqueous polymers and methods of use of such polymers for delivering in situ bioactive agents.

BACKGROUND

Materials that gel in situ have recently gained attention as promising implantable drug delivery systems as well as injectable matrices for tissue engineering. There is an emerging need for materials that are biocompatible, promote cellular proliferation and biosynthesis, support physiological loads, and are easily manipulated and synthesized. Materials that gel in situ are promising as they are easily handled and permit cell seeding; they offer the ability to form any desired implant shape, and may be engineered to be biodegradable and biocompatible.

In situ gelation is the bases of injectable systems that eliminate the need for surgical procedures and offers the advantage of the ability to form any desired implant shape. The change in molecular association can be driven by changes in temperature, pH, or solvent composition. Among the candidates of stimuli sensitive systems, organic solvent-free injectable systems are designed by using the thermosensitive sol-to-gel transition of aqueous solution. Such a system enables bioactive agents to be easily entrapped.

To perform as an ideal injectable system, the aqueous solution of a polymer should exhibit low viscosity at formulation conditions and gel quickly at physiological conditions. Considering the biomedical applications, the biocompatibility of the polymers is also an important issue. Therefore, the material should be biodegradable, and by keeping water-rich hydrogel properties it should not induce tissue irritation during the degradation.

In situ gelling of aqueous Poloxamer 407 and N-isopropylacrylamide copolymers have been studied as candidate materials for injectable drug delivery systems and also tissue engineering applications. These materials are, however, non-biodegradable and animal studies demonstrated an increase in triglyceride and cholesterol after intraperitoneal injection of the aqueous Poloxamer 407 solution.[9]

Other reported thermogelling drug delivery materials include N-isopropylacryl amide copolymers, poly(acrylic acid)-g-POLOXAMER (SMART GEL), chitosan/glycerol phosphate, and poly(ethylene glycol)/poly(lactic acid-co-glycolic acid). Aqueous solutions of such materials undergo sol-to-gel transitions with increasing temperatures. A formulation having a sol-phase at a relatively low temperature and a gel-phase at body temperature is preferable for an injectable, in-situ gel-forming depot for drug delivery and tissue engineering applications.

Recently, Jeong et al. reported biodegradable, in situ gelling poly(ethylene glycol-b-(DL-lactic acid-co-glycolic acid)-b-ethylene glycol), (PEG-PLGA-PEG), triblock copolymers. (See U.S. Pat. No. 6,117,949) They exhibited promising properties as an injectable drug delivery system. In vivo studies in rats demonstrated that the copolymer gels were still present after one month. During the degradation, the initially transparent gel became opaque due to preferential mass-loss of hydrophilic PEG rich segments. This change in morphology and the generation of an interface or phase might denature the protein drugs or cause cell deterioration in tissue engineering. In vitro release of porcine growth hormone (PGH) and insulin from the in-situ formed gel stopped after releasing 40–50% of loaded proteins.

Recently, several protein/peptide drugs demonstrated excellent efficacy in clinical trials and have been introduced to the market. With the advent of genetic engineering, proteins/peptides will soon become much more common drugs. However, due to the short plasma half-life and instability of proteins, there are urgent needs for suitable delivery vehicles. Certain drug formulations need a one to two-week delivery system. Moreover, a one to two-day delivery system may be required. For example, ifosfamide, a drug used for germ cell testicular cancer, is administered intravenously for 5 consecutive days. This treatment is repeated every three weeks or after recovery from hematological toxicity. In order to prepare such a short-term delivery system, poly(ethylene glycol) grafted with poly(lactic acid-co-glycolic acid) (PEG-g-PLGA), where hydrophilic PEG is a backbone, is designed. This material is expected to show a different gelation and degradation behavior, and consequently, a different drug release profile as compared to PEG-PLGA-PEG.

The following references disclose processes or compounds useful in this art:
U.S. Pat. No. 5,702,717
U.S. Pat. No. 5,117,949
Hill-West, J. L.; Chowdhury, S. M.; Slepian, M. J.; Hubbell, J. A. *Proc. Natl. Acad. Sci. USA,* 1994, 91, 5967–5971.
Stile, R. A.; Burghardt, W. R.; Healy, K. E. *Macromolecules,* 1999, 32, 7370–7379.
Chen, G. H.; Hoffman, A. S.; *Nature,* 1995, 373, 49–52.
Thomas, J. L.; You, H.; Tirrell, D. *J. Am. Chem. Soc.,* 1995, 117, 2949–2950.
Malstom, M.; Lindman, B. *Macromolecules,* 1992, 25, 5446–5450.
Yang, J.; Pickard, S.; Deng, N. J.; Barlow, R. J.; Attwood, D.; Booth, C. *Macromolecules,* 1994, 27, 670–680.
Jeong, B.; Bae, Y. H.; Lee, D. S.; Kim, S. W. *Nature,* 1997, 388, 860–862.
Johnston, T. P.; Punjabi, M. A.; Froelich, C. *J. Pharm. Res.,* 1992, 9(3), 425–434.
Wout, Z. G. M.; Pec, E. A.; Maggiore, J. A.; Williams, R. H.; Palicharla, P.; Johnston, T. P. *J. Parenteral Sci. & Tech.,* 1992, 46(6), 192–200.
Jeong, B.; Bae, Y. H.; Kim, S. W. *J. Controlled Releases,* 2000, 63, 155–163.
Jeong, B.; Bae, Y. H.; Kim, S. W. *J. Biomed. Mater. Res,* 2000, 50 (2), 171–177.
Jeong, B.; Gutowska, A. J. Am. Chem. Soc., 2000, Submitted.
Jeong, B. Unpublished Data. 2000.
IFEX Prescription, http://www.ifex.com/ifpre.html, A Bristol-Meyers Squibb Co., Princeton, N.J. 08543
Bellare, J. R.; Davis, H. T.; Scriven, L. E.; Talmon, Y. *J. Electron Microsc. Tech.* 1988, 10, 87–111.
Wanka, G.; Hoffmann, H.; Ulbricht, W. *Colloid Polym. Sci.,* 1990, 268, 101–117.
Tanodekaew, S.; Godward, J.; Heatley, F.; Booth, C. *Macromol. Chem. Phys.,* 1997, 198, 3385–3395.

Odian, G. In *Principles of Polymerization*, 2$^{nd}$ ed.; John Wiley & Sons, Inc. Korean Student Ed.: Korea, 1981; p 513.

Alexandrisdis, P.; Holzwarth, J. F.; Hatton, T. A. *Macromolecules*, 1994, 27, 2414–2425.

Discher, B. M.; Won, Y.-Y.; Ege, D. S.; Lee, J. C. M.; Bates, F. S.; Discher, D. E.; Hammer, D. A. *Science*, 1999, 284, 1143–1146.

Won, Y.-Y.; Davis, H. T.; Bates, F. S. *Science*, 1999, 283, 960–963.

Brown, W.; Schillen, K.; Almgren, M.; Hvidt, S.; Bahadur, P. *J. Phys. Chem.*, 1991, 95, 1850–1858.

Cau F.; Lacelle, S. *Macromolecules*, 1996, 29, 170–178.

Jeong, B.; Bae, Y. H.; Kim, S. W. *Colloids and Surfaces B: Biointerfaces*, 1999, 16: 185–193.

Zhou, Z.; Chu, B. *J. colloid and Interface Science*, 1988, 126(1): 171–180.

Deng, Y.; Yu, G. E.; Price, C.; Booth, C. *J. Chem. Soc. Faraday Trans.* 1992, 88(10), 1441–1446.

Yu, G. E.; Deng, Y.; Dalton, S.; Wang, Q. G.; Attwood, D.; Price, C.; Booth, C. *J. Chem. Soc., Faraday Trans.* 1992, 88 (17), 2537–2544.

Jeong, B.; Bae, Y. H.; Kim, S. W. *Macromolecules* 1999, 32, 7064–7069.

Israelachivili, J. N. *Intermolecular and Surface Forces*, Academic Press, New York, 1985.

Feil, H.; Bae, Y. H.; Feijen, J.; Kim, S. W. *Macromolecules*, 1993, 26, 2496–2500.

Jeong, B.; Lee, D. S.; Shon, J. I.; Bae, Y. H.; Kim, S. W. *J. Polym. Sci. Polym. Chem.* 1999, 37, 751–760.

SUMMARY

The present invention provides a thermogelling biodegradable aqueous polymer solution with a polyethylene glycol (PEG) block and a biodegradable polyester block, where the blocks are linked to form a polymer of a general structure comprising the formula of $A_n(B)$, where n is greater than 2 and A is selected from the group consisting of a polyethylene glycol block and a biodegradable polyester block, B is selected from the group consisting of a polyethylene glycol block and a biodegradable polyester block, and A is different from B.

It is an object of the present invention to provide a thermogelling biodegradable polymer solution having utility as a bioactive agent delivery system.

A further object of this invention is to provide a drug delivery system that can be injected parenterally.

Another object of this invention is to provide a drug delivery system that allows control of polymer degradation rate or duration of a sustained gel by controlling the number of branches linked to the backbone of the structure or by mixing a first polymer comprising the formula $A_n(B)$ with at least one other polymer comprising the formula $A_n(B)$, wherein the first polymer is different from said at least one other polymer.

Still another object of this invention is to provide a drug delivery system that allows control of the stability of drugs and drug dosage from one day to two months.

Another object of this invention is to provide block copolymer drug delivery systems that are biodegradable.

Still another object of this invention is to provide block copolymer drug delivery systems that demonstrate desirable release rates.

Another object of this invention is to provide injectable block copolymer drug delivery systems that are in solution at room temperature or lower and gel at or about physiological temperature.

Yet another object of this invention is to provide injectable drug delivery systems that eliminate the need for surgical procedures and offers the advantage of the ability to form any desired implant shape.

Still another object of this invention is to provide stimuli sensitive, organic solvent-free injectable drug delivery systems that are designed by using the thermosensitive sol-to-gel transition of aqueous solutions.

Yet another object of this invention is to provide an aqueous solution of a polymer that exhibits low viscosity at formulation conditions and gels quickly at physiological conditions.

Still yet another object of this invention is to provide drug delivery systems that can provide desired release rates by varying the ratio of polyethylene glycol (PEG) block and a biodegradable polyester block.

Additional objects and advantages of this invention will become apparent from the following summary and detailed description of the various embodiments making up this invention.

There is an emerging need for materials that are biocompatible, promote cellular proliferation and biosynthesis, support physiological loads, and are easily manipulated and synthesized. Materials that gel in situ are promising as they are easily handled, permit cell seeding, and they offer the ability to form any desired implant shape. The present invention is well suited for delivery of cells, whereby the thermogelling biodegradable aqueous polymer solution provides a scaffold for tissue repair and organ regeneration. The present invention offers several advantages including: the flowability of the thermogelling biodegradable aqueous polymer solutions can fill any shape of a defect, promotion of tissue integration, easily incorporates live cells and various therapeutic agents (e.g. growth factors), and finally enables minimally invasive placement.

Therefore, another object of this invention is to provide a thermogelling biodegradable polymer solution having utility in tissue engineering.

Still another object of this invention is to provide a thermogelling biodegradable polymer solution having utility as a cell delivery system.

Yet still another object of this invention is to prepare biodegradable solubilizes for hydrophobic drugs. Due to surfactant nature of the PEG-g-PLGA and PLGA-g-PEG, this polymer can be used as a solubilizer for hydrophobic drug formulations.

Biodegradable thermogelling polymers based on PEG-g-PLGA generate lactic acid and glycolic acid, during degradation. Therefore, these polymers may not be suitable for delivery of certain acid sensitive therapeutic agents. Further, PLGA's vulnerability to hydrolysis may require that the sol-gel formulations be stored at refrigerator (about 4–10° C.) or freezer (about 0° C.) temperatures.

To accommodate the need of acid sensitive therapeutic agents, further disclosed is a polymer, drug-delivery system comprising, in part, an enzymatically biodegradable polypeptide. Specifically, disclosed are polypeptide polymer systems, such as polypeptide/polyethylene glycol block copolymers, for use as biodegradable, thermosensitive gelling drug delivery systems. A peptide bond is more stable against hydrolysis than is an ester bond, thus, the polypeptide/polyethylene glycol copolymer systems provide superior storage stability. For example, a polymer system as disclosed herein including a degradable polypeptide is storable as a water solution. The PEG-PLGA polymers must be stored at low temperatures due to their tendency toward hydrolysis; additionally, such polymers are thick pastes, making them difficult to handle. The polypeptide polymers, such as the polypeptide/polyethylene glycol block copolymers form powders.

The degradation of the polypeptide system is accelerated only by proteolytic enzymes, so degradation occurs only after in-vivo injection. Degradation products of the polypeptide polymer systems, such as the polypeptide/polyethylene glycol copolymer system, are neutral amino acids. Thus, pH drops during degradation may be avoided and acid-sensitive proteins/cells are protected.

For a clear and concise understanding of the specification and claims, including the scope given to such terms, the following definitions are provided:

Bioactive Agent: As used herein, a "bioactive agent" shall mean any drug, molecule, biomolecule, or cell.

Drug: As used herein, a "drug" shall mean any organic compound or substance having bioactivity and adapted or used for a therapeutic purpose.

Polypeptide: As used herein when referring to a therapeutic agent, bioactive agent, drug, or the like to be delivered by a carrier system, a "polypeptide" shall mean any peptide, polypeptide, oligopeptide, and/or protein used as a drug and shall not be limited by molecular weight, sequence, length, activity or use.

Parenteral: Administering into the body or administered in a manner other than through the digestive tract, as by intravenous or intramuscular injection.

BRIEF DESCRIPTION OF THE DRAWINGS

A more complete appreciation of the invention will be readily obtained by reference to the following description and the accompanying drawings in which like numerals in different figures represent the same structures or elements, wherein.

DETAILED DESCRIPTION

Figure 1:
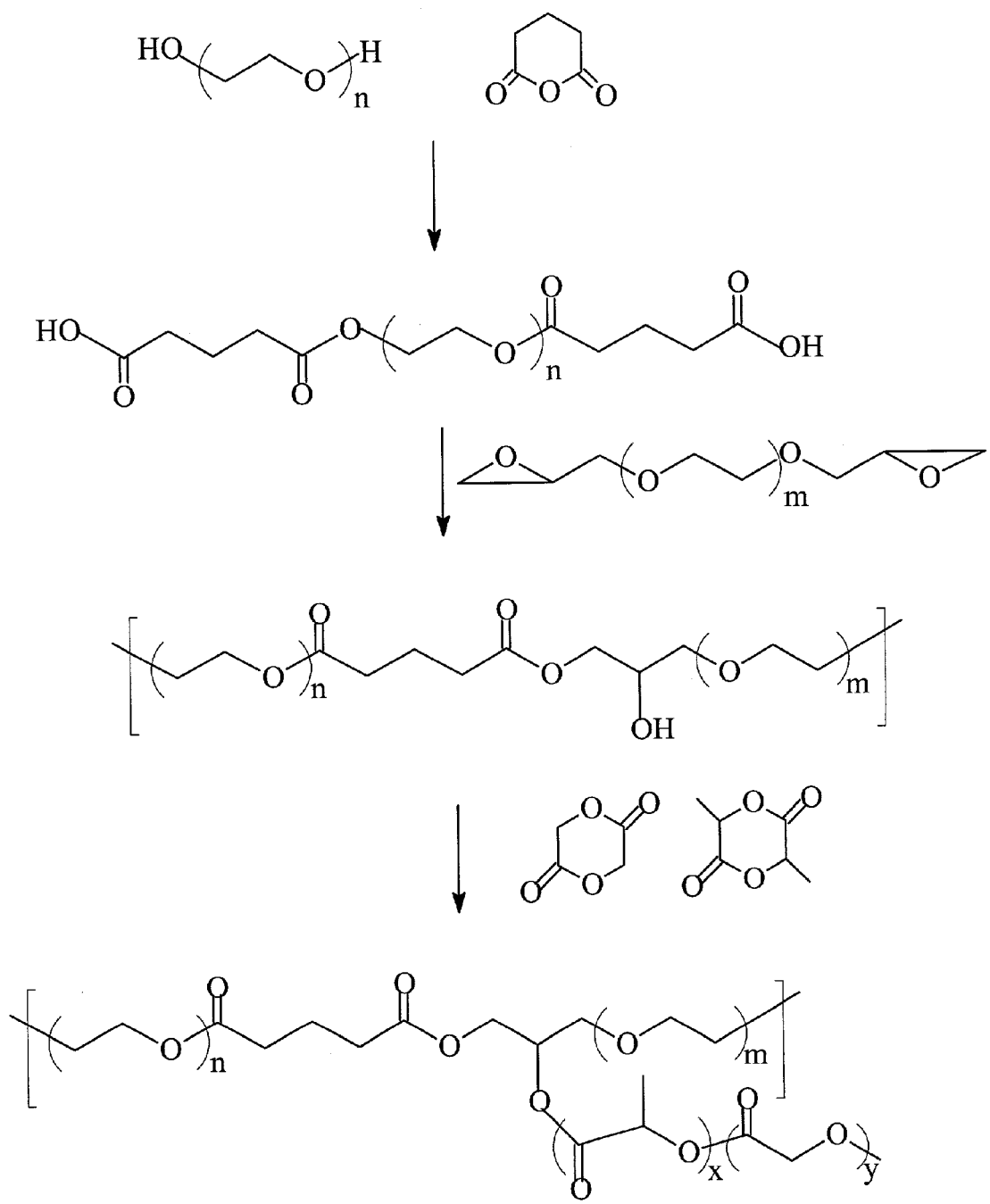
FIG. 1 is a schematic representation of the synthesis of PEG-g-PLGA.

The present invention is a biodegradable polymer solution, comprising a polyethylene glycol (PEG) block, and a biodegradable polyester block linked to form a polymer of a general structure comprising the formula of $A_n(B)$, where n is greater than 2 and A is selected from the group consisting of a polyethylene glycol block and a biodegradable polyester block, B is selected from the group consisting of a polyethylene glycol block and a biodegradable polyester block, and A is different from B.

The present invention further provides a thermogelling biodegradable aqueous polymer solution which comprises a biodegradable polymer solution, comprising a polyethylene glycol (PEG) block, and a biodegradable polyester block linked to form a polymer of a general structure comprising the formula of $A_n(B)$, where n is greater than 2 and A is selected from the group consisting of a polyethylene glycol block and a biodegradable polyester block, B is selected from the group consisting of a polyethylene glycol block and a biodegradable polyester block, and A is different from B, and an aqueous solution.

The thermogelling biodegradable aqueous polymer solution is preferred when prepared with the formula $A_n(B)$ as described previously and n is between 3 and 10.

The biodegradable polyester block is preferably a member selected from the group consisting of poly(DL-lactic acid), poly(L-lactic acid), poly(glycolic acid), poly(ε-caprolactone), poly(γ-butyrolactone), poly(α-valerolactone), poly(β-hydroxybutyric acid), and their copolymers or terpolymers. It is also preferred that the copolymers and/or terpolymers are selected from the group consisting of poly(DL-lactic acid-co-glycolic acid), poly(L-lactic acid-co-glycolic acid), poly(ε-caprolactone-co-DL-lactic acid), copoly(ε-caprolactone-co-DL-lactic acid-glycolic acid). The above listing of suggested biodegradable polyester blocks is not intended to be all-inclusive. The biodegradable polyester blocks can have a maximum molecular weight of 100,000 with a preferred range of about 1,000 and 30,000, and most preferably between about 1,000 and 10,000. The biodegradable polyester blocks are limited as a result of the desire to accommodate a solubility limit and not because of degradability It is preferred that the polyethylene glycol (PEG) block have an average molecular weight of between about 300 and 20,000 and is more preferably between about 500 and 10,000. The PEG block with a higher molecular weight than 10,000 is hard to be filtered through glomeruli filtration.

The present invention provides an effective biodegradable bioactive agent delivery liquid, comprising an effective amount of bioactive agent contained in thermal gelling biodegradable aqueous polymer solution comprising a polyethylene glycol (PEG) block, and a biodegradable polyester block linked to form a polymer of a general structure comprising the formula of $A_n(B)$, where n is greater than 2 and A is selected from the group consisting of a polyethylene glycol block and a biodegradable polyester block, B is selected from the group consisting of a polyethylene glycol block and a biodegradable polyester block, and A is different from B.

It is understood that the present invention can make use of any bioactive agent, which can be any drug, molecule, biomolecule, or cell. As well, the present invention can provide as a delivery system for other matter requiring a sustained release rate.

The thermogelling biodegradable aqueous polymer solutions of the present invention are useful as drug delivery systems that provide as a carrier for drugs. A drug is an organic compound or substance having bioactivity and adapted or used for a therapeutic purpose including but not limited to anti-cancer agents, hormones, antibiotics, narcotic antagonists, analgesics, anti-inflammatory agents, anti-depressants, anti-epileptics, anti-malarial agents, immunoactivators, growth factors, gene therapy agents, oligonucleotides, therapeutic peptides and proteins, and combinations thereof. In particular, the present invention provides a very useful delivery system for polypeptide and protein drugs that require a short biodegradation period to accommodate the requirement for a specific sustained release rate due to the short plasma half-life and instability.

Because the polymers of the present invention are composed of hydrophobic and hydrophilic blocks and the surfactant nature, this polymer can be used as a solubilizer for hydrophobic drug formulations. This property enables these polymers to be used as a solubilizer of hydrophobic drugs. Typical cancer drugs, such as Taxol, have good efficacy while they tend to have low solubility in water. The polymers of the present invention can be used as biocompatible solubilizers for such drugs.

The present invention is well suited for delivery of anti-cancer agents. It is preferred that the anti-cancer agents be selected from the group consisting of adriamycin, mitomycin, bleomycin, cisplatin, carboplatin, doxorubicin, daunorubicin, 5-fluouroacil, methotrexate, taxol, taxotere, and actinomycin D. It is understood that other anti-cancer agents may work as well with this invention and the preceding list is not meant to be all-inclusive.

The present invention is equally well suited for delivery of polypeptides. It is preferred that that polypeptides be selected from the group consisting of oxytocin, vasopressin, adrenocorticotropic growth factor (PDGF), prolactin, luliberin or luteinising hormone releasing hormone (LHRH), growth hormone, growth hormone releasing factor, insulin, somatostatin, glucagons, interleukin-2 (IL-2), interferon-α, β,γ (IFN-α,β,γ), gastrin, tetragastrin, pentagastrin, urogastroine, secretin, cacitonin, enkephalins, endorphins, angiotensins, thyrotropin releasing hormone (TRH), tumor necrosis factor (TNF), nerve growth factor (NGF), granulocyte-colony stimulating factor (G_CSF), granulocyte macrophage-colony stimulating factor (M-CSF), rennin, bradykinin, bacitracins, polymixins, colistins, tyrocidin, gramicidines, and synthetic analogues, modifications and pharmacologically active fragments thereof, monoclonal antibodies and soluble vaccines. This list is not all-inclusive and it is understood that other proteins can be used as well.

The present invention is well suited for delivery of cells. The thermogelling biodegradable aqueous polymer solution comprising cells provides a scaffold for tissue repair and organ regeneration as well as for therapeutic use.

A useful aspect of the present invention is method for the delivery of a bioactive agent in a thermogelling polymer matrix to a warm-blooded animal for the controlled release of the bioactive agent. Fundamental to this aspect of the invention is to provide an injectable thermogelling biodegradable aqueous polymer solution which comprises a polyethylene glycol (PEG) block, a biodegradable polyester block, wherein the blocks are linked to form a polymer of a general structure comprising the formula of An(B), where n is greater than 2 and A is selected from the group consisting of a polyethylene glycol block and a biodegradable polyester block, B is selected from the group consisting of a polyethylene glycol block and a biodegradable polyester block, and A is different from B. The thermogelling biodegradable aqueous polymer solution is then mixed with an effective amount of a bioactive agent to form a polymer-bioactive agent mixture, maintained at a temperature below the gelling temperature of the polymer, and provided into a warm blooded animal to form a gel depot as the temperature is raised by the body temperature of the animal to be above the gelling temperature of the polymer. It is recognized that this aspect of the present invention can have various forms of application. For example, it is well suited to use this method of application when it is desired to apply a bioactive agent to a warm-blooded animal during a surgical procedure where a portion of the body of the warm-blooded animal is exposed. By applying the polymer-bioactive agent mixture to an area exposed during surgery will allow the formation of a depot to a specific/desired area.

Another aspect of the present invention is method for the parenteral delivery of a bioactive agent in a thermogelling polymer matrix to a warm-blooded animal for the controlled release of the bioactive agent. Fundamental to this aspect of the invention is to provide an injectable thermogelling biodegradable aqueous polymer solution which comprises a polyethylene glycol (PEG) block, a biodegradable polyester block, wherein the blocks are linked to form a polymer of a general structure comprising the formula of An(B), where n is greater than 2 and A is selected from the group consisting of a polyethylene glycol block and a biodegradable polyester block, B is selected from the group consisting of a polyethylene glycol block and a biodegradable polyester block, and A is different from B. The injectable thermogelling biodegradable aqueous polymer solution is then mixed with an effective amount of a bioactive agent to form a polymer-bioactive agent mixture, maintained at a temperature below the gelling temperature of the polymer, and injected into a warm blooded animal to form a gel depot as the temperature is raised by the body temperature of the animal to be above the gelling temperature of the polymer. This aspect of the invention provides well when it is desired to provide a bioactive agent under controlled release without having to surgically expose a warm-blooded animal. Several injectable routes including intradermal or intracutaneous, subcutaneous or hypodermic, intramuscular, intravenous, and intraspinal can administer the polymer-bioactive agent mixture parenterally.

Having described the invention, the following experimental examples are given. These specific examples are not intended to limit the scope of the invention described in this application.

Experimental Section:

Materials:

DL-lactide (Polyscience) and glycolide (Polyscience) were recrystallized from ethyl acetate. Glutaric anhydride (Aldrich), glutaric acid (Aldrich), stannous octoate (Aldrich), epoxy terminated polyethylene glycol (m.w.: 600; Polyscience), poly(ethylene glycol m.w.: 1000; Aldrich), and 1,6-diphenyl-1,3,5-hexatriene (DPH; Aldrich) were used as received.

Synthesis: Three-step Synthesis of PEG-g-PLGA (FIG. 1.)

First, PEGs (m.w.=1000, 38.28 g, 38.28 mmole) were dissolved in 90 ml toluene. Toluene was then distilled off to a final volume of 50 ml to remove water by azeotropic distillation. Carboxylic acid terminated PEG (CPEG) was prepared by reacting PEG with excess amount of glutaric anhydride in the presence of catalytic amounts of glutaric acid. Glutaric anhydride (7.255 g, 80.39 mmole) and glutaric acid (0.042 g, 0.40 mmole) were added and the reaction mixture was stirred at 120° C. for 6 hours. The chemical shifts (ppm) in the spectra are 1.9 (central methylene of glutarate), 2.4 (methylene of glutarate next to carbonyl group), 3.6 (ethylene of PEG), and 4.2 (methylene of PEG connected to glutarate). The one to one area ratio of the peaks at 1.9 ppm and 4.2 ppm indicates the quantitative end group functionalization. Diethyl ether was added to the reaction mixture to precipitate out the carboxylic acid terminated PEG (CPEG). The product was placed under high vacuum (~$10^{-3}$ mm Hg) for 48 hours to remove the residual solvent.

Figure 2:
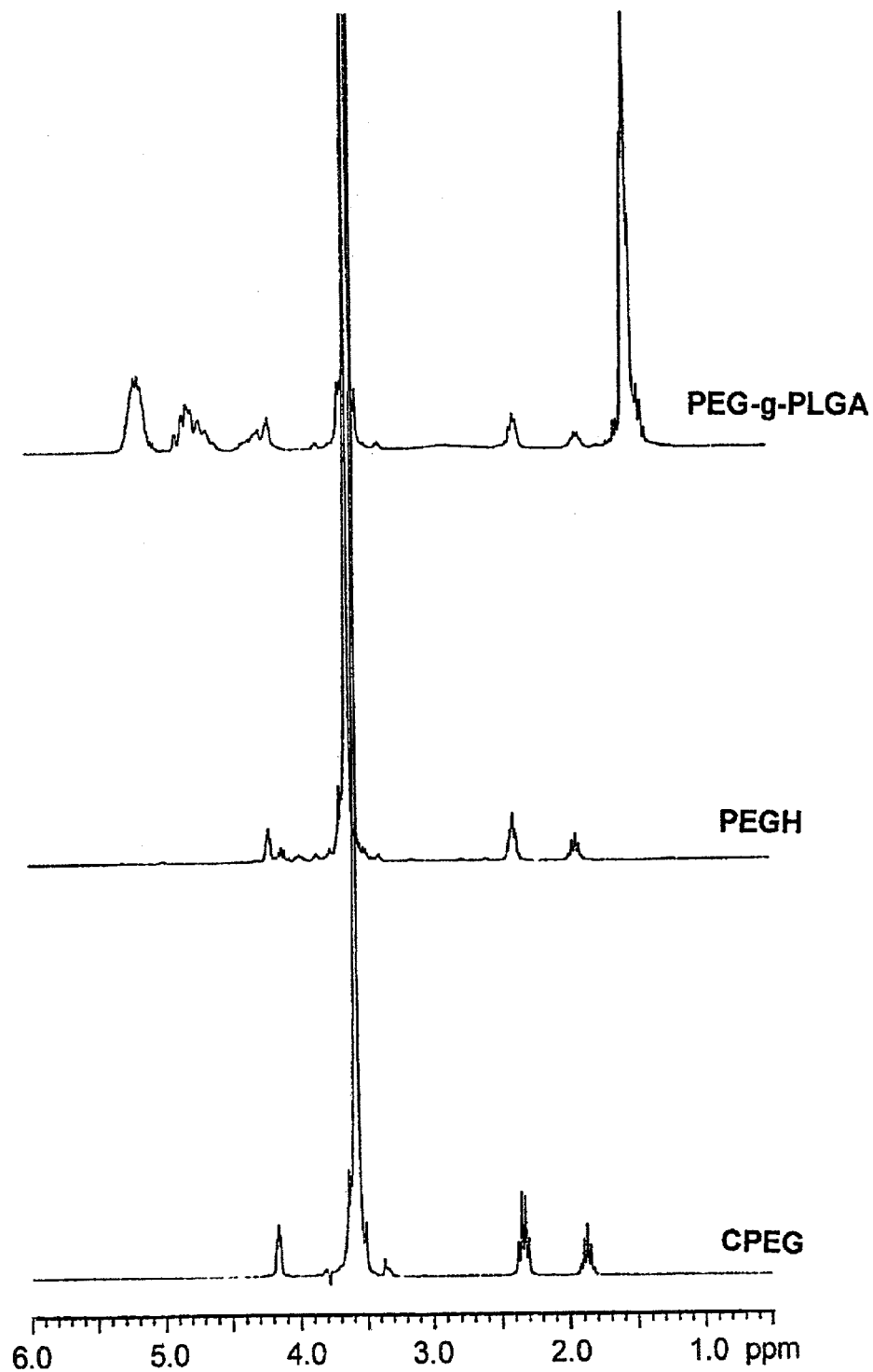
FIG. 2 is a graphical representation of Nuclear Magnetic Resonance (NMR) spectra of intermediate and final products of PEG-g-PLGA synthesis.

In the second step, epoxy terminated PEG (EPEG) (m.w.=600, 5.619 g, 9.36 mmole) was reacted with CPEG (11.50 g, 9.36 mmole) in toluene at 120° C. for 24 hours to prepare PEG with pendant hydroxyl groups (PEGH) along the PEG backbone. The weight average molecular weight ($M_w$) and polydispersity index (PDI) of resulting PEGH, which were determined by GPC, was 3000 and 1.3 relative to polystyrene standards. The peaks at 1.9 ppm and 2.4 ppm come from glutarate. The peaks at 3.6 ppm and 4.3 ppm come from PEG. The small overlapped peaks 3.4 to 4.2 ppm of PEGH come from the connecting methylene or methine moieties between CPEG and EPEG (FIG. 2).

In the third step, DL-lactide (19.2 g, 133.3 mmole) and glycolide (6.4 g, 55.1 mmole) were polymerized in situ on the preformed PEGH backbone at 130° C. for 24 hours, using stannous octoate (76 µL, 0.187 mmole) as a catalyst. The graft copolymers were precipitated into excess ethyl ether and the residual solvent was removed under vacuum.

Figure 3:
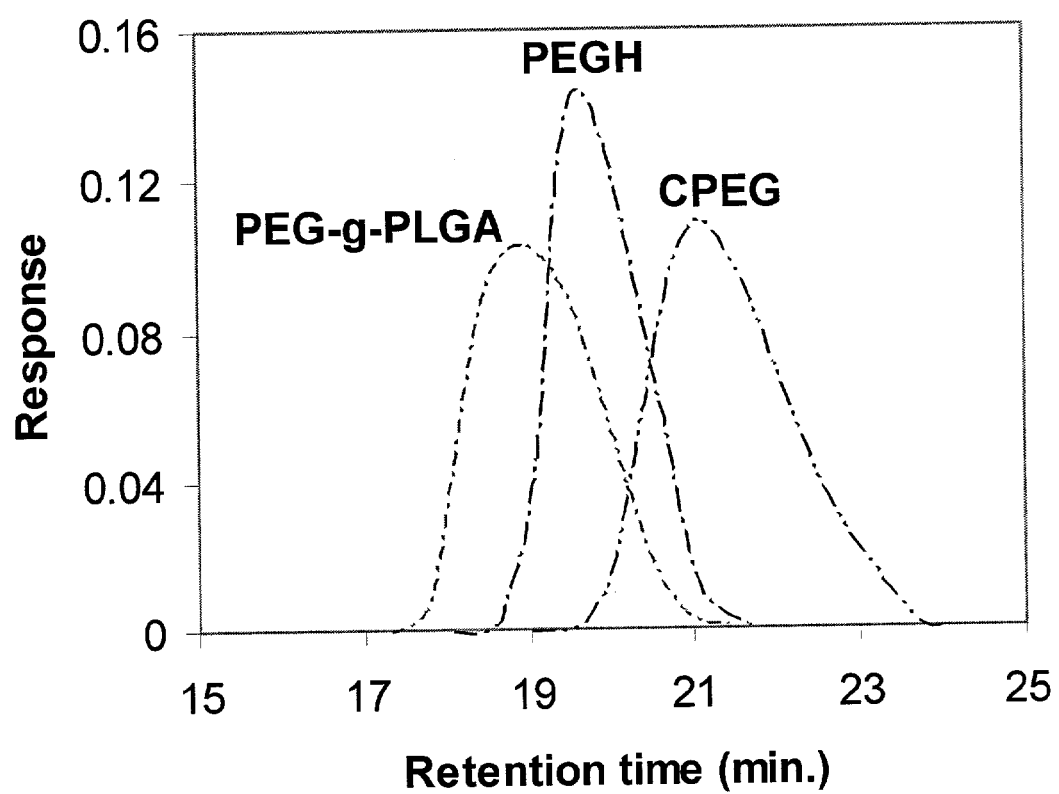
FIG. 3 is graphical representation of a Gel Permeation Chromatography (GPC) chromatogram of polymers showing progress of reactions.

There are two possibilities of the ring-opening pattern of the epoxy group during the reaction of EPEG and CPEG. The nucleophiles prefer to attack the sterically less hindered side of the epoxy group in the base-catalyzed addition, while ring opening is less regiospecific in cationic polymerization. The GPC chromatogram in FIG. 3 shows the increase in molecular weight by the formation of PEGH from CPEG and EPEG. Assuming a PEGH molecular weight of about 3,000, there are ~2–3 pendant hydroxy groups per each PEGH.

The resultant PEGH was used as an initiator for the ring-opening polymerization of DL-lactide and glycolide in the presence of stannous octoate as a catalyst. H-NMR spectra (FIG. 2) show an ethylene glycol unit at 3.6 ppm, a lactic acid unit at 5.3 ppm (methine) and 1.8 ppm (methyl), and a glycolic acid unit at 4.8 ppm. Composition of the PEG-g-PLGA calculated by $^1$H-NMR was 2.98/2.35/1.00 (ethylene glycol/DL-lactic acid/glycolic acid) in mole ratio. The methylene protons of the epoxy group show up at 2.6 ppm and 2.8 ppm in H-NMR. In the H-NMR spectrum of PEGH and PEG-g-PLGA the epoxy signals are too small to be analyzed quantitatively. Weight average molecular weight ($M_w$) and PDI of PEG-g-PLGA determined by GPC relative to polystyrene standards was 11,000 and 1.3 respectively.

Gel Permeation Chromatography (GPC):

The GPC system (Waters 515) with a refractive Index Detector (Waters 410) and a Light Scattering Detector Mini Dawn (Wyatt Technology) were used to obtain molecular weight and molecular weight distribution. Styragel® HMW 6E and HR 4E columns (Waters) were used in series. Tetrahydrofuran (THF) was used as an eluting solvent.

Cryo-Transmission Electron Microscope (Cryo-TEM):

Using cryo-TEM, a 1% PEG-g-PLGA solution was investigated in the form of vitreous films. Detailed procedures for the sample preparation have been published elsewhere. (Bellare et. al., *Electron Microsc. Tech.* 1999, 10, 87–111.) The liquid films of 10 to 300 nm thickness freely spanning across the micropores in a carbon-coated lacelike polymer substrate were prepared at 23.7° C. with complete control of temperature and humidity, and rapidly vitrified with liquid ethane at its melting temperature (–180° C.). Imaging was performed using a JEOL 1210 operating at 120 kV. Adequate phase contrast was obtained at a nominal underfocus of ~6 micrometers. Images were recorded on a Gatan 724 multiscan camera, and optical density gradients in the background were digitally corrected.

CMC Determination:

Hydrophobic dye, 1,6-diphenyl-1,3,5-hexatriene (DPH) was dissolved in methanol with a concentration of 0.4 mM. This solution (20 µL) was injected using a microsyringe into 2.0 ml PEG-PLGA polymer aqueous solution with various concentrations between 0.0032 and 0.26 wt. % and equilibrated for 5 hours at 4° C. UV-VIS spectrometer (HP 8453) was used to get the UV-VIS spectra in the range of 280 to 450 nm at 20° C. CMC was determined by the plot of the difference in absorbance at 377 nm and at 391 nm ($A_{377}$–$A_{391}$) versus logarithmic concentration.

Viscosity:

The viscosity of PEG-g-PLGA aqueous solution (22 wt. %) was measured as a function of temperature. A Canon-Fenske viscometer 200 with a viscometer constant of 0.0966 centistokes/sec. was used to measure the viscosity of the polymer solution.

Dynamic Mechanical Analysis:

The sol-gel transition of the graft copolymer aqueous solution (22 wt. %) was investigated using a dynamic mechanical rheometer (Rheometric Scientific: SR 2000). The polymer solution was placed between parallel plates having a diameter of 25 mm and a gap distance of 0.5 mm. The data were collected under controlled stress (4.0 dyne/$cm^2$) and frequency of 1.0 radian/second. The heating and cooling rate was 0.2° C./min.

Sol-Gel Transition:

The sol-gel transition was determined by a test tube inverting method with a temperature increment of 1° C. per step. Polymer aqueous solutions (0.5 g) were prepared in 4 mL vials with inner diameters of 11 mm. The vials were immersed in a water bath at each step for 15 minutes. The sol-gel transition temperature was monitored by inverting the vials, and if there was no flow in 30 seconds, it was regarded as a gel. The transition temperature was determined with ±1° C. accuracy.

NMR Study:

A NMR spectrometer (Varian® VXR 300) was used for $^1$H-NMR and $^{13}$C-NMR to study composition and microenvironment change during sol-to-gel transition. For the $^{13}$C-NMR in $D_2O$, a 22 wt. % PEG-g-PLGA solution was prepared.

Results and Discussion

Micellization:

PEG-g-PLGA is an amphiphilic copolymer and a core-shell structure can be expected in water. The hydrophobic PLGA side chains form a core and the hydrophilic PEG backbones form a shell region. The formation of core-shell structure was investigated by Cryo-transmission electron microscopy (Cryo-TEM) and dye solubilization method.

Figure 4:
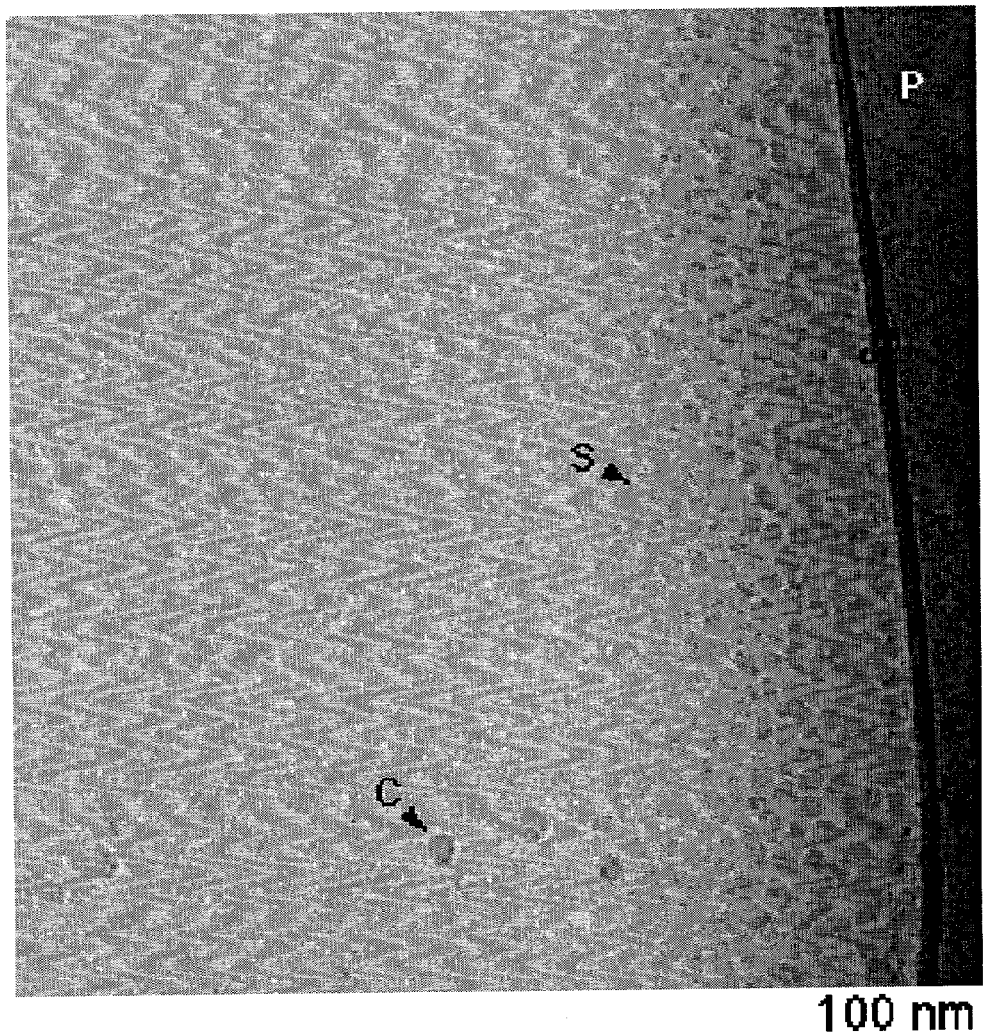
FIG. 4 is a Cryo-Transmission Electron Microscope (TEM) image showing micelle formation of the PEG-g-PLGA polymer at a concentration of 1 wt % in water at 23.7° C.

The formation of micelles was directly confirmed by a Cryo-TEM image. An 1 wt. % PEG-g-PLGA solution at 23.7° C. was quenched into a vitrified form at −180° C. The Cryo-TEM image shows closely packed spherical micelles (denoted as S in FIG. 3) on the left side of black stripe. The diameter of a micelle is about 9 nm. (FIG. 4)

Figure 5A:
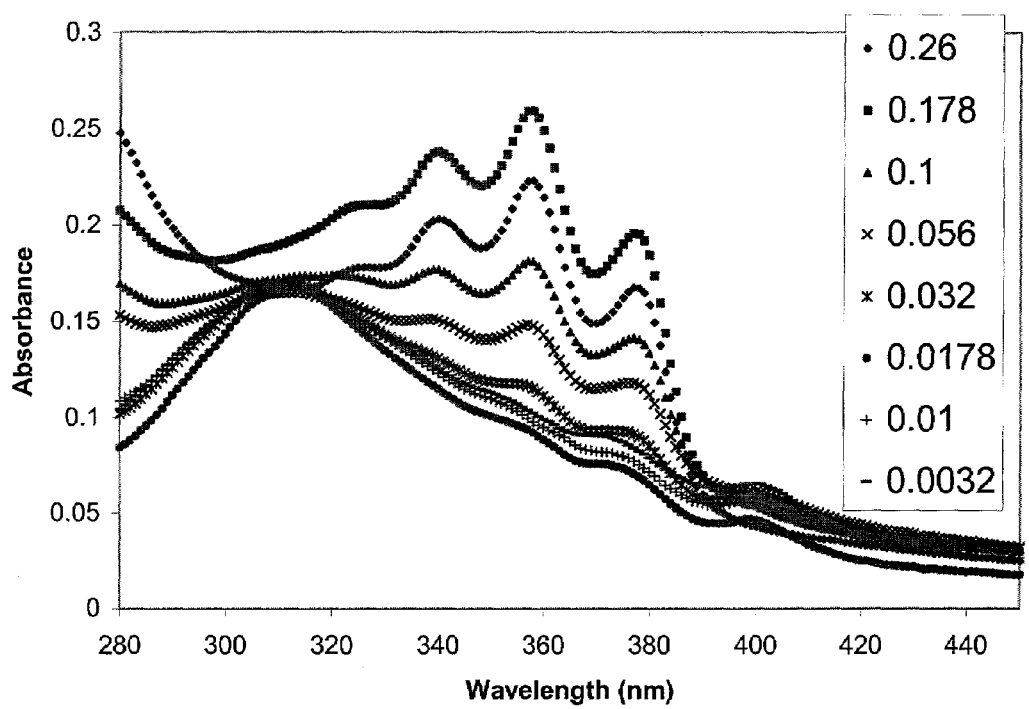
FIG. 5a is a graphical representation of UV spectra showing the formation of core-shell structure of polymers in water at 20° C. where diphenyl-1,3,5-hexatriene (DPH) concentration was fixed at 4 µM and polymer concentration varied according to key legend.
Figure 5B:
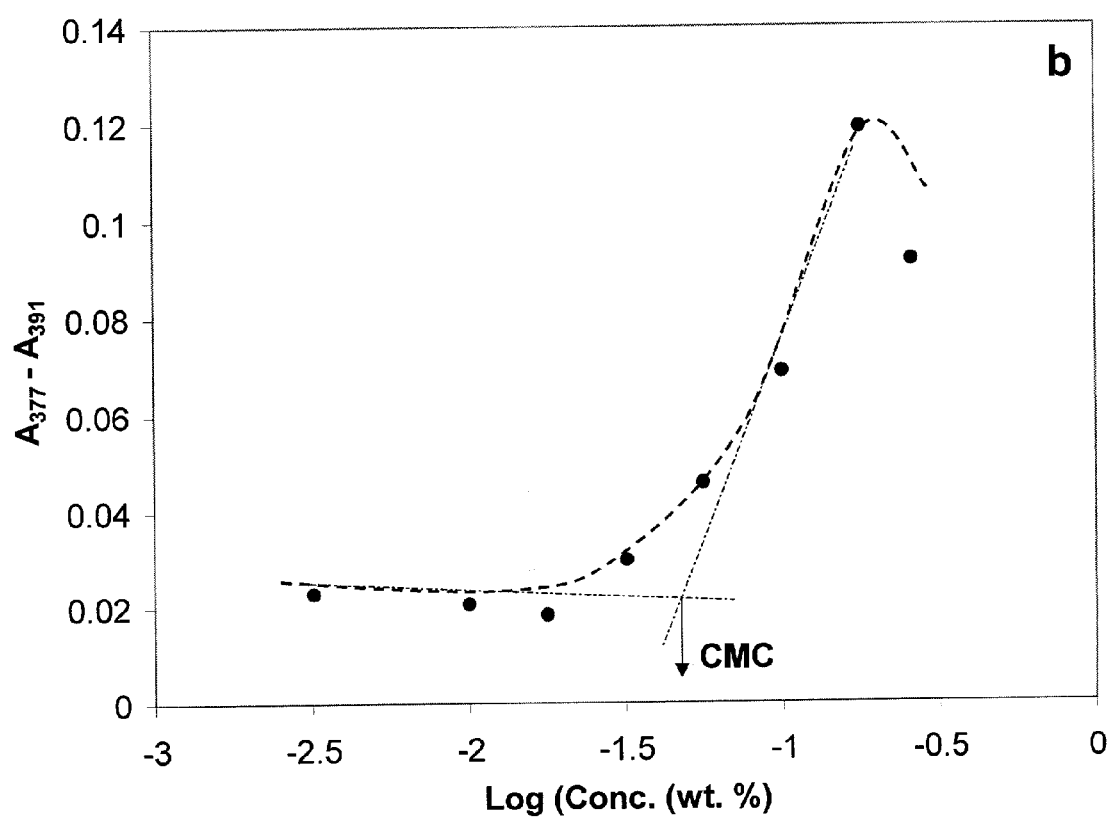
FIG. 5b is a graphical representation of the cmc determination by extrapolation of the difference in absorbance at 377 and 392 nm.

At a fixed concentration of DPH, the polymer concentration was increased from 0.0032 to 0.26 wt. %. The absorption coefficient of the hydrophobic dye (DPH) is much higher in a hydrophobic environment than in water. Thus, with increasing polymer concentration, the absorbance at 377 and 356 nm increased, indicating that the polymers formed a core-shell structure in water creating a hydrophobic environment (FIG. 4-a). The critical micelle concentration (CMC) was determined by extrapolating the absorbance at 377 nm minus absorbance at 391 nm ($A_{377}-A_{391}$) versus logarithmic concentration (FIG. 4-b) to compensate for the scattering effect. The CMC value determined by this extrapolation is not precise due to the uncertainty in the line, but it is in a range of 0.01–0.05 wt. % at 20° C. FIG. 5a is a UV spectrum showing the formation of core-shell structure of polymers in water at 20° C. DPH concentration was fixed at 4 μM and polymer concentration varied: 0.0032, 0.01, 0.0178, 0.032, 0.056, 0.010, 0.178, 0.26 wt. %. The increase in absorption band at 377 nm with increasing polymer concentration indicates the formation of a hydrophobic environment, that is, micelles, in water. FIG. 5b shows a CMC determination by extrapolation of the difference in absorbance at 377 nm and at 391 nm.

Sol-Gel Transition:

At high concentrations, the PEG-g-PLGA aqueous solution undergoes a sol-to-gel transition with increasing temperature. The viscosity of a 22 wt. % PEG-g-PLGA aqueous solution that was measured by Cannon-Fenske viscometer was 27 centipoises at 20° C. This viscosity is low enough for an easy formulation of the polymer with pharmaceutical agents that could be injected using a 22-gauge needle. Above the gelation temperature, the viscosity is too high to flow through the capillary of this viscometer. Dynamic mechanical analysis of 22 wt. % aqueous polymer solutions show that the real part (η') of complex viscosity increases from 5 to 500 dyne sec cm$^{-2}$ [P] and elastic modulus (G') increased from zero to 100 dyne cm$^{-2}$ during a sol-to-gel transition (FIG. 6). η' and G' are measures of dissipated energy and stored energy respectively when a material is subject to cyclic deformation. And, practically no flow was observed above 30° C. in the test-tube inverting method, indicating a sol-to-gel transition. When we compare the two methods for 22 wt % aqueous polymer solutions, the gelation temperature determined by test-tube inverting method corresponds to the temperature at which η' of 100 P and G' of 50 dyne/cm$^2$ are reached in dynamic mechanical analysis when thermal equilibrium is assumed in both cases.

Figure 6:
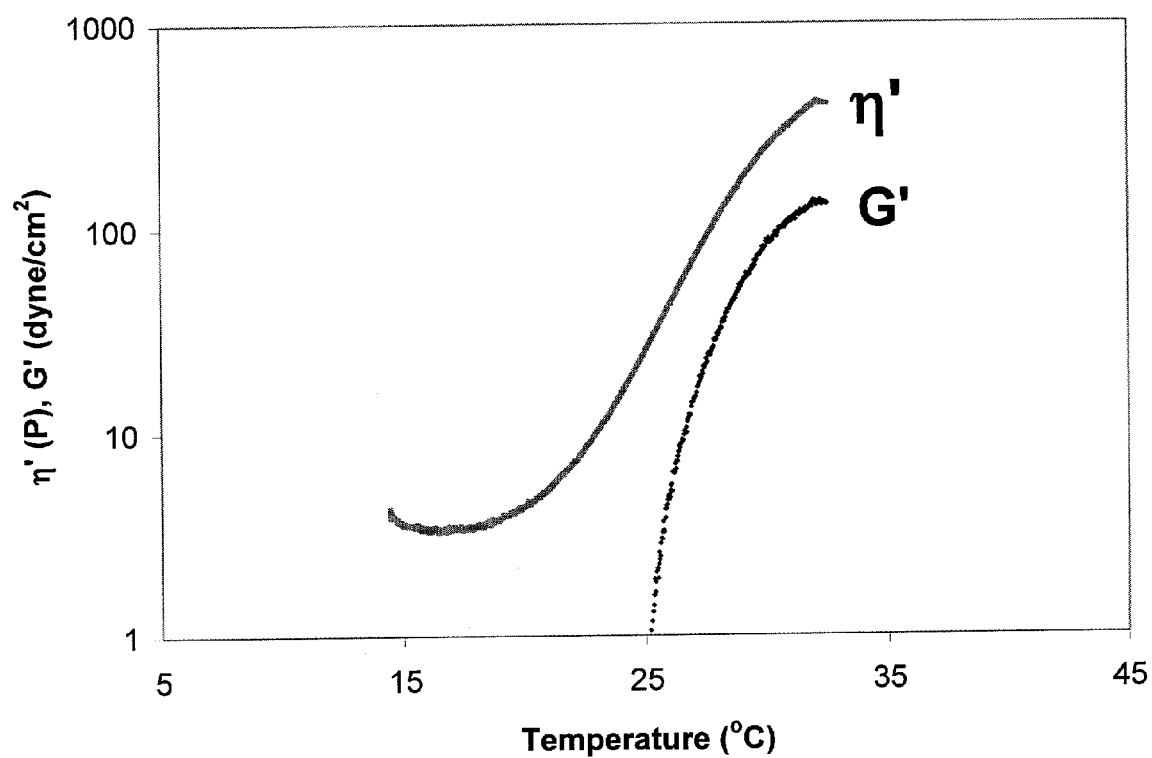
FIG. 6 is a graphical representation of real part (n') of complex viscosity and elastic modulus (G') of 22 wt % PEG-g-PLGA aqueous solutions as a function of temperature.

The phase diagram of PEG-g-PLGA aqueous solutions determined by a test-tube inverting method is shown in FIG. 6. The sol-to-gel transition is accompanied by a sharp increase in viscosity. The critical gel concentration (CGC) above which the gel phase appears was about 16 wt. %. Below CGC, the system flows even though the viscosity increases as the temperature increases. The sol-to-gel transition temperature, estimated at about 30° C., was slightly affected by the polymer solution concentration. The presence of the gel phase around body temperature (37° C.) indicates that the material is a promising candidate for an injectable drug delivery system that can be formulated at room temperature, and would form a gel in situ upon subcutaneous or intramuscular injection. The pharmaceutical agents would then be slowly released from the in situ formed gel.

Figure 7:
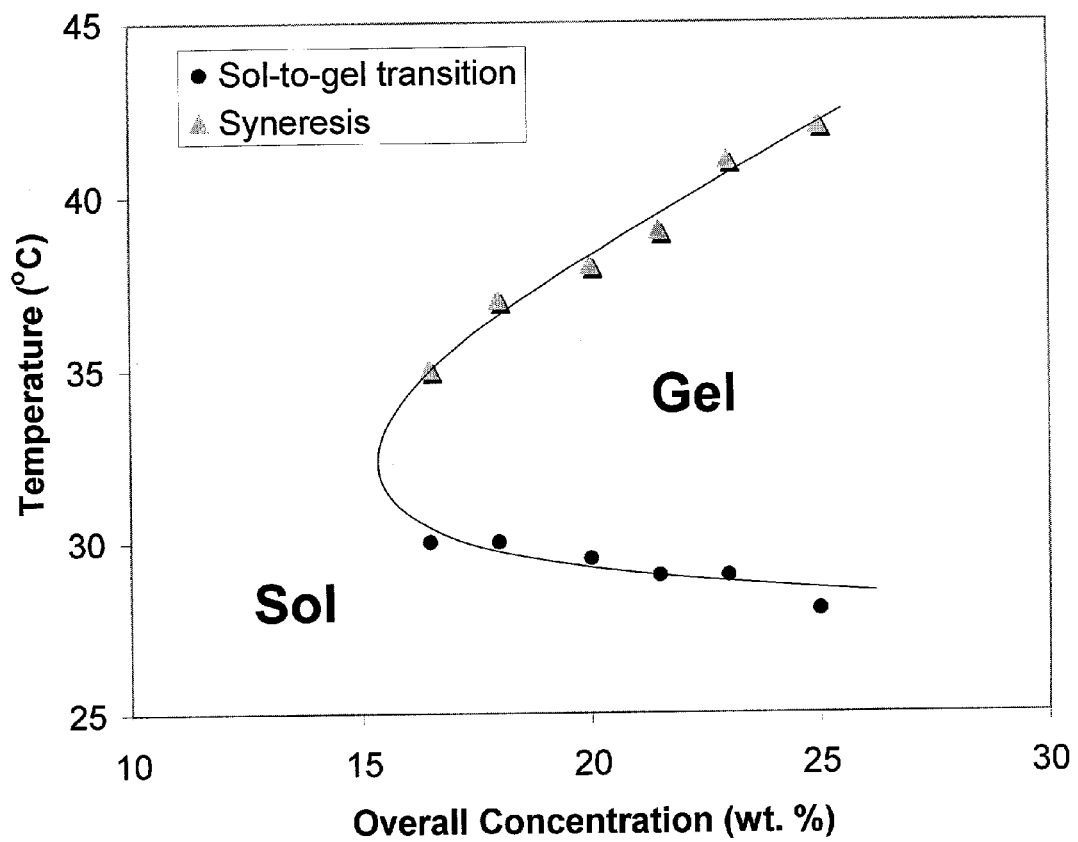
FIG. 7 is a graphical representation of a phase diagram of PEG-g-PLGA aqueous solution.

Further analysis of the phase diagram illustrates that with increasing temperature the gel exhibits syneresis, marked as gray triangles in FIG. 7, a macromolecular phase separation where some amount of water is exuded from the gel phase. Above the syneresis temperature, the gel phase remains separated from the water. Therefore, the sol phase at low temperature is a homogeneous one-phase solution while the sol phase above syneresis is a two-phase system. The gel region, right side of the trend line in the phase diagram indicates the area where a uniform gel phase exists. Based on the phase diagram (FIG. 7), 21–25 wt. % of PEG-g-PLGA aqueous solutions are recommended as injectable formulations for drug delivery.

Figure 8:
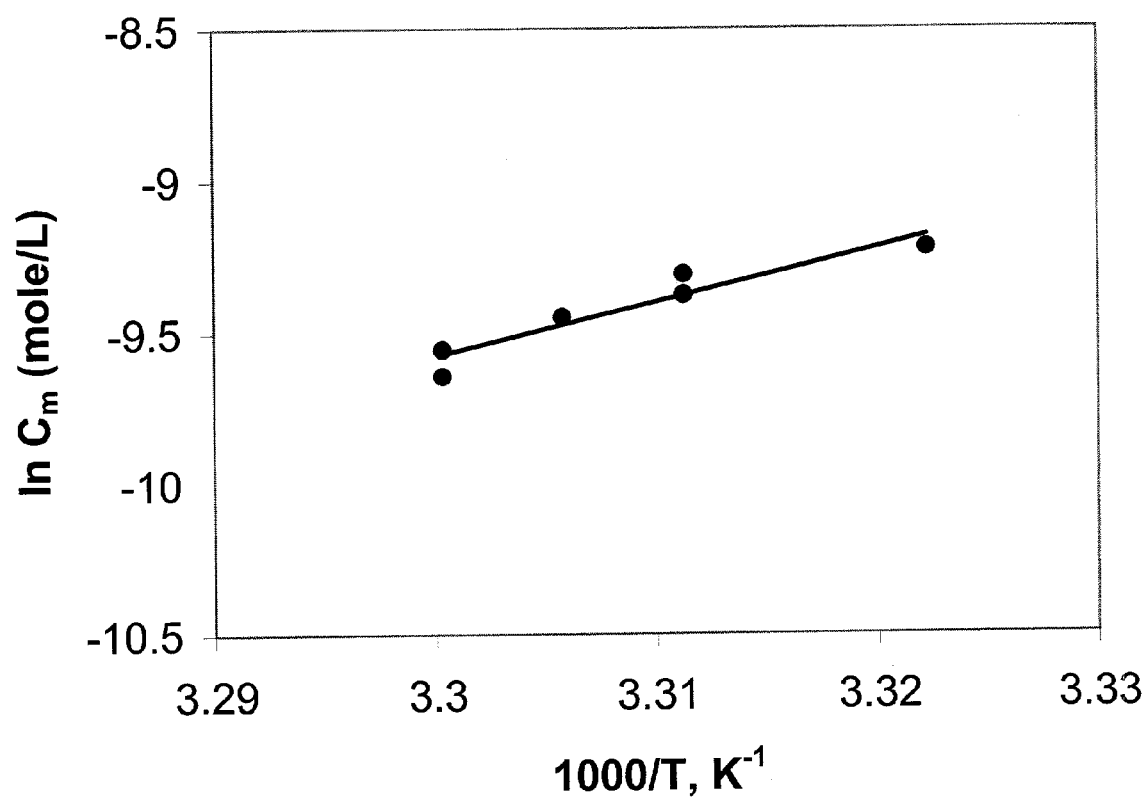
FIG. 8 is a graphical representation of the calculation of enthalpy of sol-to-gel transition of PEG-g-PLGA aqueous solutions.

The aggregation number of a micelle can be estimated from the size of the micelle by assuming that the micelle is a hard sphere. The radius of a micelle can be estimated from equation.

a. $R=(3M_{s,D}.v_2/4\pi N_A)^{1/3}$

Where $M_{s,D}$ denotes the molecular weight of a micelle obtained from centrifugal sedimentation, which is close to weight average molecular weight ($M_w$). $v_2$, and $N_A$ are the partial specific volume of the polymer, and the Avogadro's number, respectively. The aggregation number of a micelle ($N_{ag}$) is given by equation.

b. $N_{ag}=M/M_0$

Where M and Mo denote molecular weight of a micelle and molecular weight of a polymer respectively. Assuming $v_2$ is 0.95, which is typical for polyester or polyether, and R is about 4.5 nm (diameter~9 nm) from Cryo-TEM, the micellar aggregation number is 40 at 20° C. The aggregation number of a micelle is assumed to be practically constant for a sol region as in the cases of PEG-PLGA-PEG and poloxamer 407. This calculation also assumes that M is equal to $M_{s,D}$ and the molecular weight of PEG-g-PLGA ($M_0$) is 6000 as determined from GPC data. Based on this estimation, the thermodynamic functions such as enthalpy ($\Delta H^0$), Gibbs free energy ($\Delta G^0$), and entropy of gelation ($\Delta S^0$) can be calculated. Now, the standard states of gelation process are taken to be the micelles in ideal dilute solution at unit molarity and micelles in gel state.

c. $\Delta G^0 = RT_{gel} \ln C_m$ d. $\Delta H^0 = R[d \ln C_m/d(1/T_{gel})]$ e. $\Delta S^0 = (\Delta G^0 - \Delta H^0)/T_{gel}$ $C_m$ is the concentration of micelles in mole L$^{-1}$ that is calculated by assuming that the aggregation number per micelle is 40. $T_{gel}$ is the sol-to-gel transition temperature. $\Delta H^0$ calculated from the slope of $\ln C_m$ versus $1/T_{gel}$ (FIG. 8) is 146 kJ mole$^{-1}$ (micelle) or $\Delta H^0 = 3.65$ kJ mole$^{-1}$ (chain). This value is similar to gelation of poloxamer 407 ($\Delta H^0 = 1.5$ kJ mole$^{-1}$ (chain)) and PEG-PLGA-PEG triblock copolymers ($\Delta H^0 = 1.32$ kJ mole$^{-1}$ (chain)). Gibbs free energy ($\Delta G^0$) and entropy ($\Delta S^0$) for the gelation of 22 wt. % PEG-g-PLGA aqueous solution with a $T_{gel}$ of 30° C. are −0.59 kJ mole$^{-1}$ and 1.9 J mole$^{-1}$ K$^{-1}$, respectively. This calculation leads to the conclusion that the entropy drives the gelation. The molecular origin of such an entropy-driven process has been suggested as hydrophobic interactions. Water molecules tend to surround the hydrophobic segment (PLGA) to decrease the free energy. Consequently, the entropy of water molecules decreases in the presence of hydrophobes. Therefore, the surface area of hydrophobic molecules is minimized in water. Such hydrophobic interactions increase with increasing temperature, and change the molecular conformation of PEG-g-PLGA, thus might drive the gelation.

Figure 9:
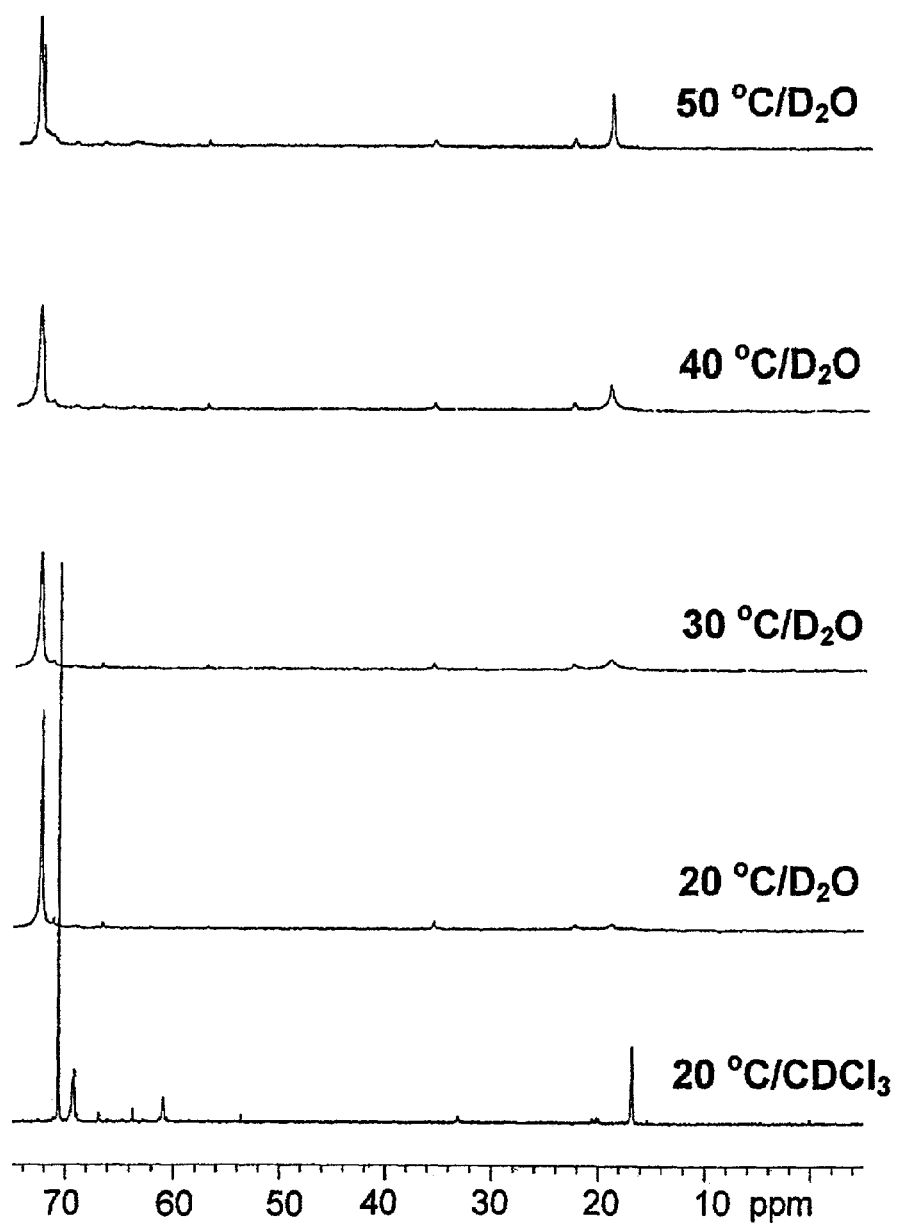
FIG. 9 is a graphical representation of the $^{13}$C-NMR spectra of PEG-g-PLGA in $D_2O$ (22 wt. %) as a function of temperature.

The $^{13}$C-NMR analysis of the polymers was conducted at different temperatures to elucidate the structure of the gel and mechanism of gel formation (FIG. 9). Spectra of polymers dissolved in water and chloroform were compared. The $^{13}$C-NMR spectra of a 22 wt. % PEG-g-PLGA in D$_2$O were obtained at 20 (sol state), 30 (just above sol-to-gel transition), 40 (gel state), and 50° C. (macrophase-separated state) by simply increasing the temperature around the probe without changing NMR parameters. The equilibration time at each temperature was 15 minutes. Chloroform (CDCl$_3$) is a nonselective good solvent for both PEG and PLGA blocks while water (D$_2$O) is a good solvent for PEG but is a poor solvent for PLGA. The sharp peaks of both PEG and PLGA in chloroform are compared with a collapsed peak of PLGA in water at first and second rows of $^{13}$C-NMR, indicating core (PLGA)-shell (PEG) structure of the polymer in water. The molecular motion of PEG in water is decreased due to anchoring effects by the hydrophobic PLGA segments compared with that in chloroform. This fact is reflected in a broadened peak of PEG in D$_2$O at 20° C. The change in molecular association at sol-to-gel transition involves the change in molecular motion of the polymers. The change in $^{13}$C-NMR with increasing temperature (20° C.–50° C.) shows such a change in microenvironment around the PEG and PLGA. The PEG peak (72 ppm) at a gel state (30° C.) is broadened and decreased by half in height compared with a sol state (20° C.), whereas there is a slight increase in PLGA peak height (20 ppm) at gel state (30° C.). These changes in peak heights indicate a significant decrease in molecular motion of the PEG backbone, and increased thermal motions of the PLGA side chains during sol-to-gel transition. This behavior is quite different from that of PLGA-g-PEG. PLGA-g-PEG showed little change in PEG peak during sol-to-gel transition at the $^{13}$C-NMR in D$_2$O. Based on these observations, the following model can be suggested for the sol-to-gel transition of PEG-g-PLGA copolymer aqueous solutions. In a sol state, the polymer conformation is micellar where the PEGs occupy shell and PLGAs occupy core of the micelle. The degree of association in a sol state is not enough to form a three dimensional network. With increasing temperature, the hydrophobic interactions increase and associations of polymers decrease the PEG molecular motion, resulting in a long-range network formation, that is, a gel. The degree of association is strong enough to keep its integrity in the presence of excess water at a given temperature such as 37° C. Therefore, we can define this system as a gel rather than a solution with an increased viscosity. As the temperature increases further, the long-range interactions among the polymers increase and phase mixing between PEG and PLGA occurs, resulting in the macrophase separation between water and polymer that occurs at 50° C.

The 22 wt. % polymer solutions (0.5 g) are injected into 4 mL vials (diameter of 1.1 cm) and kept in a 37° C. water bath for five minutes. During this time the gel forms. 3 mL of phosphate buffer saline (37° C., pH=7.4) is added and the vials are shaken (16 strokes/minute) in the water bath to simulate body condition. The gel keeps its integrity for one-week in vitro, and the initially turbid gel becomes transparent in 3 to 7 days. After 7 days, the gel totally disintegrated to become a clear polymer solution.

This material can be applied for a short-term delivery of bioactive agents such as pharmaceutical drugs (e.g. proteins, anticancer drugs) as well as a carrier or delivery system for bioactive agents used in tissue engineering. The hydrophobicity of the drug and the molecular structure of the polymers affect the extent of diffusion or degradation dominant drug release profile. Therefore, by choosing the appropriate drug and molecular parameters of PEG-g-PLGA, a short-term delivery system can be designed based on this polymer hydrogel.

Synthesis: One-step Synthesis of PLGA-g-PEG

The graft copolymer PLGA-g-PEG was synthesized by a one-step ring opening polymerization of DL-lactide, glycolide, and epoxy terminated poly(ethylene glycol) (PEG; m.w.=600) using stannous octoate as a catalyst. The DL-lactic acid/glycolic acid/ethylene glycol mole ratio is 3.2/1/2.8, which was determined by H-NMR. Therefore, the grafting frequency of PEG is 4.7% by mole. Therefore, the grafting frequency of PEG is 4.7% by mole. Gel permeation chromatography (GPC) using light scattering and refractive index detectors in series can give absolute molecular weight of polymers. (P. J. Wyatte, Anal. Chim. Acta, 1993, 272, 1) GPC shows a unimodal curve. The number average molecular weight (Mn) and polydispersity (Mw/Mn) of the polymers determined by GPC using tetrahydrofuran (THF) as an eluting solvent are 9300 and 1.5, respectively. Therefore, the 4~5 PEGs are grafted on a PLGA backbone.

Sol-gel Transition:

At room temperature, viscosity of the 25 wt. % aqueous solutions is about 0.3 poise (gm$^{-1}$s$^{-1}$), which allows for injecting the solution using a 25-gauge needle. With increasing temperature, the aqueous solutions (25 wt. %) of PLGA-g-PEG undergo a sol-to-gel transition at 30° C. The gel state is traditionally defined as a non-flowing semisolid by a test-tube inversion method. In the practical application, the gel should keep its equilibrium-swollen state and not dissolve in an excess amount of solvent. Further increase in temperature of the PLGA-g-PEG aqueous solution (25 wt. %) results in a macroscopic phase-separation between gel and water, that is, syneresis occurs at 50° C.

Dynamic Mechanical Analysis:

The sol-gel transition of the graft copolymer aqueous solution was investigated using dynamic rheometry (Rheometric Scientific: SR 2000) in a similar manner to poloxamer aqueous solutions. The polymer solution was placed between parallel plates having a diameter of 25 mm and a gap distance of 0.5 mm. The data were collected under controlled stress (4.0 dyne/cm$^2$) and a frequency of 1.0 radian/second. The heating and cooling rate was 0.2° C./min. By the dynamic mechanical analysis, sol-gel transition can be identified in a more reproducible and quantitative manner than the test-tube inversion method.

Figure 10:
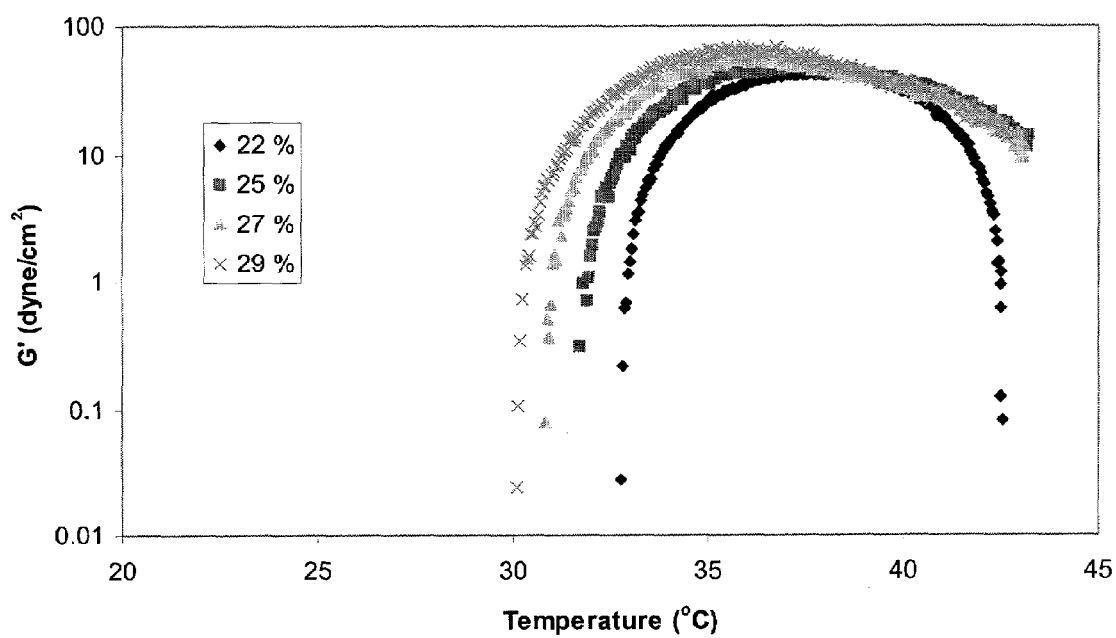
FIG. 10 is a graphical representation of the storage modulus of PLGA-g-PEG as a function of temperature and concentration.

The modulus of the PLGA-g-PEG aqueous solution is shown in FIG. 10 as a function of temperature and concentration. The storage modulus increases abruptly at the sol-to gel transition. The gels have a modulus of about 50 dyne/cm$^2$ and are slightly affected by concentration in a range of 22 to 29 wt. %. The sol-to-gel transitions occur at around 30° C., suggesting easy formulation at room temperature.

Figure 11A:
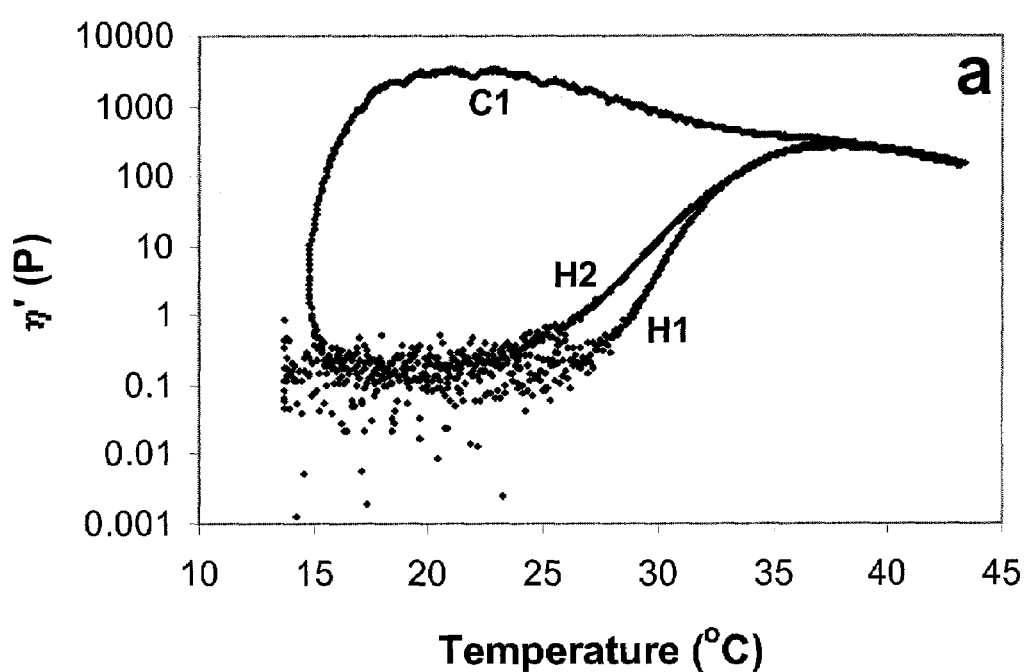
FIG. 11a is a graphical representation of a rheological study of PLGA-g-PEG copolymer aqueous solutions (25 wt. %) wherein the real part (η') of complex viscosity of the copolymer solution was measured as a function of temperature.

To confirm the reversibility of the sol-gel transition, 25 wt. % PLGA-g-PEG aqueous solutions were studied. The real part (η') of complex viscosity of the polymer solution, which is a measure of dissipated energy when cyclic deformation is applied to a material, is shown as a function of temperature in FIG. 11a. During the first heating cycle (H1), η' increased 1000 times upon sol-to-gel transition. The cooling curve (C1) shows that the gel phase persisted over the temperature range of 43~20° C. in the experimental time scale. This fact results from the difficulty in molecular rearrangement in the gel phase; once the solution forms a gel, the molecules resist disintegration. η' abruptly decreased at 15° C. due to gel-to-sol transition during the cooling of the system. The second heating curve (H2) shows sol-to-gel transition at practically the same temperature as the first heating curve (H1).

Figure 11B:
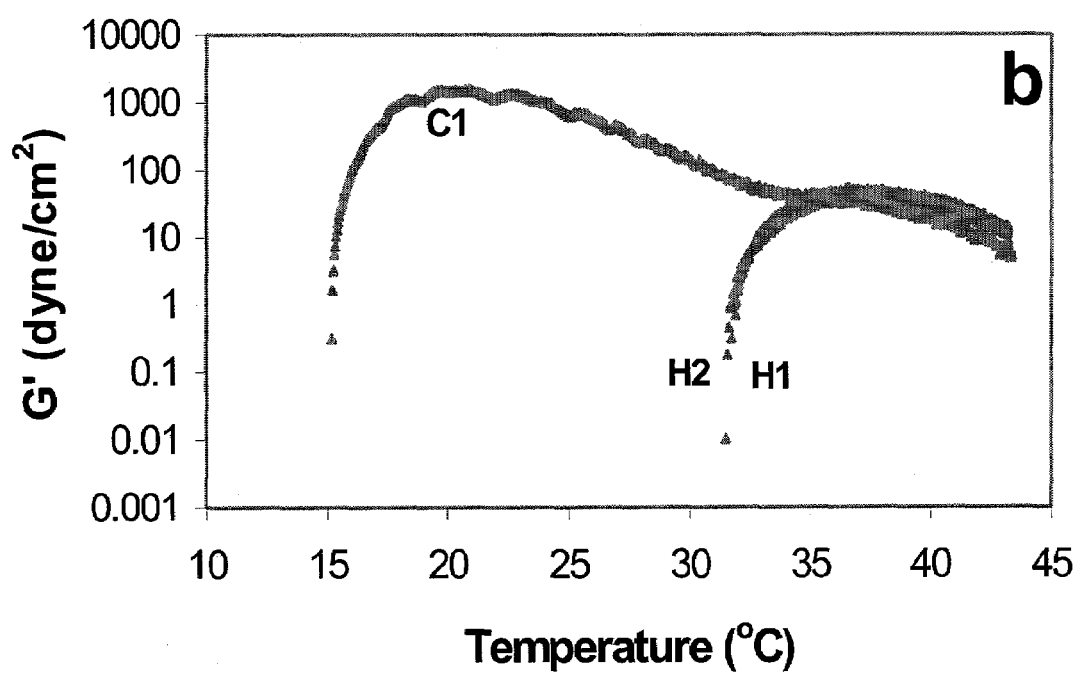
FIG. 11b is a graphical representation of a rheological study of PLGA-g-PEG copolymer aqueous solutions (25 wt. %) wherein the storage modulus (G') of the copolymer solution was measured as a function of temperature.
Figure 12:
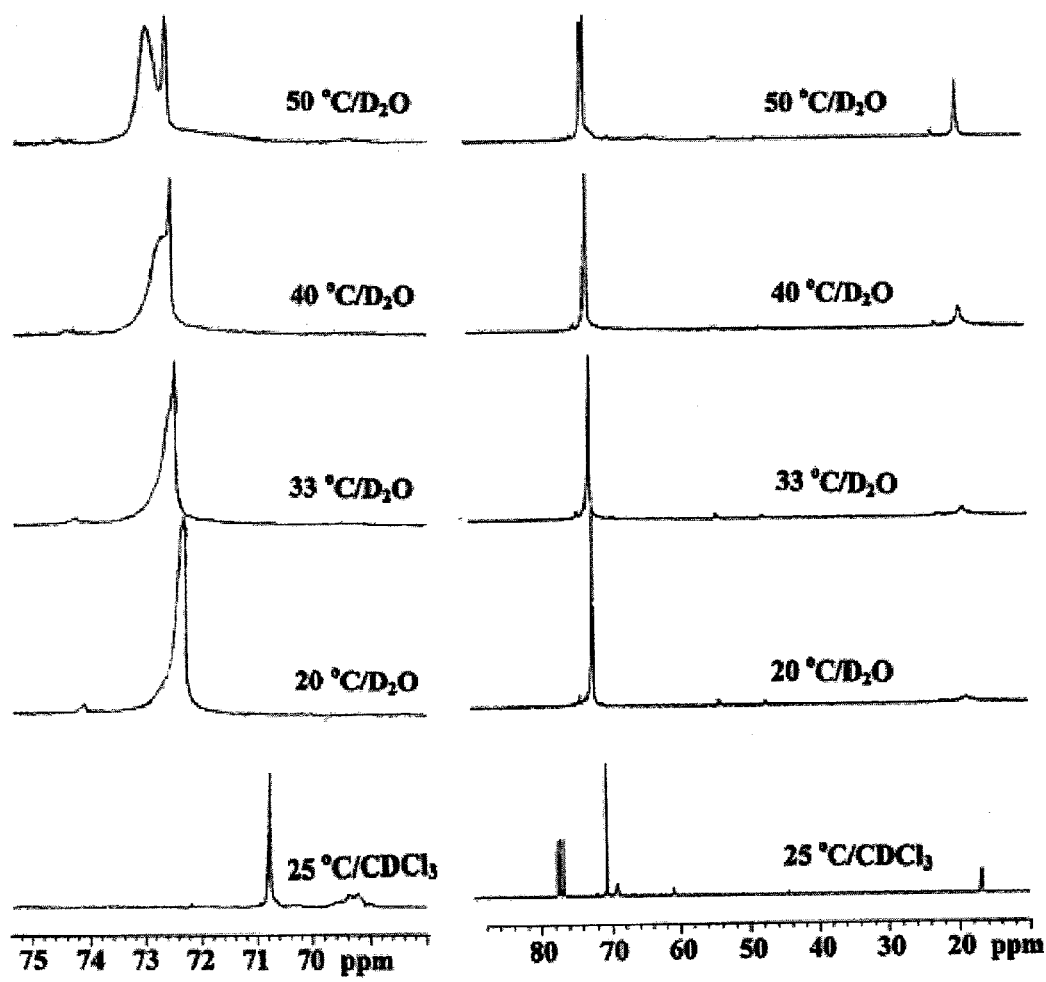
FIG. 12 is a graphical representation of a $^{13}$C-NMR (75 MHz) spectra of 25% (wt.) PLGA-g-PEG copolymer in $D_2O$ as a function of temperature wherein the zoom spectra (~73 ppm) are shown at left.

The storage moduli (G') of the PLGA-g-PEG aqueous solutions (25 wt. %), which are a measure of stored energy when a cyclic deformation is applied to a material, are practically zero at a sol state and are not shown in the heating curve (FIG. 11b; H1). G' sharply increased during sol-to-gel transition at 32° C. as shown in heating curves. The maximum value for G' was measured between 35~39° C., indicating a promising material for in-vivo (37° C.) applications. During the cooling cycle (C1), the gel modulus increased over the temperature range of 43~20° C., exhibiting similar behavior to typical elastic materials, and dropped abruptly at 15° C. due to gel-to-sol transition. During the first (H1) and second (H2) heating cycle, practically the same transition curve was measured for G', indicating a reversible gelation. The decrease in G' at temperatures above 40~45° C. can be expected due to increase in thermal motion. This trend was also observed with $^{13}$C-NMR spectra (FIG. 12).

NMR Study:

The $^{13}$C-NMR spectra of a 25 wt. % copolymer solution in D$_2$O were recorded at different temperatures. In the sol state (20° C.), the methyl peak of the hydrophobic PLGA (18 ppm) is collapsed and broadened compared with PEG peak (72 ppm) whereas that in CDCl$_3$ appears as a sharp peak, indicating core-shell structure of this polymer in water. The core-shell structure of these amphiphilic copolymers was also confirmed by micelle formation in diluted aqueous solutions. The critical micelle concentration (CMC) determined by a dye solubilzation method was 0.03 wt. % at 20° C.

Just above the sol-to-gel transition temperature (33° C.) of an aqueous PLGA-g-PEG copolymer solution (25 wt. %), the $^{13}$C-NMR peak shapes of both the hydrophobic PLGA methyl peak and hydrophilic PEG peak are preserved except that the PEG peak was shifted down field about 0.3 ppm. With a further increase in temperature, the peak height of the PLGA methyl peak increases, and the PEG peak is split into two peaks, a sharp one at 72.4 ppm and a broad one at 72.7 ppm. These behaviors are thought to be caused by an increase in molecular motion of the hydrophobic backbone and phase mixing between PEG and PLGA. The phase mixing between PEG and PLGA or PLLA was previously reported. Further increase in temperature resulted in macrophase separation between water and the polymer.

Figure 13:
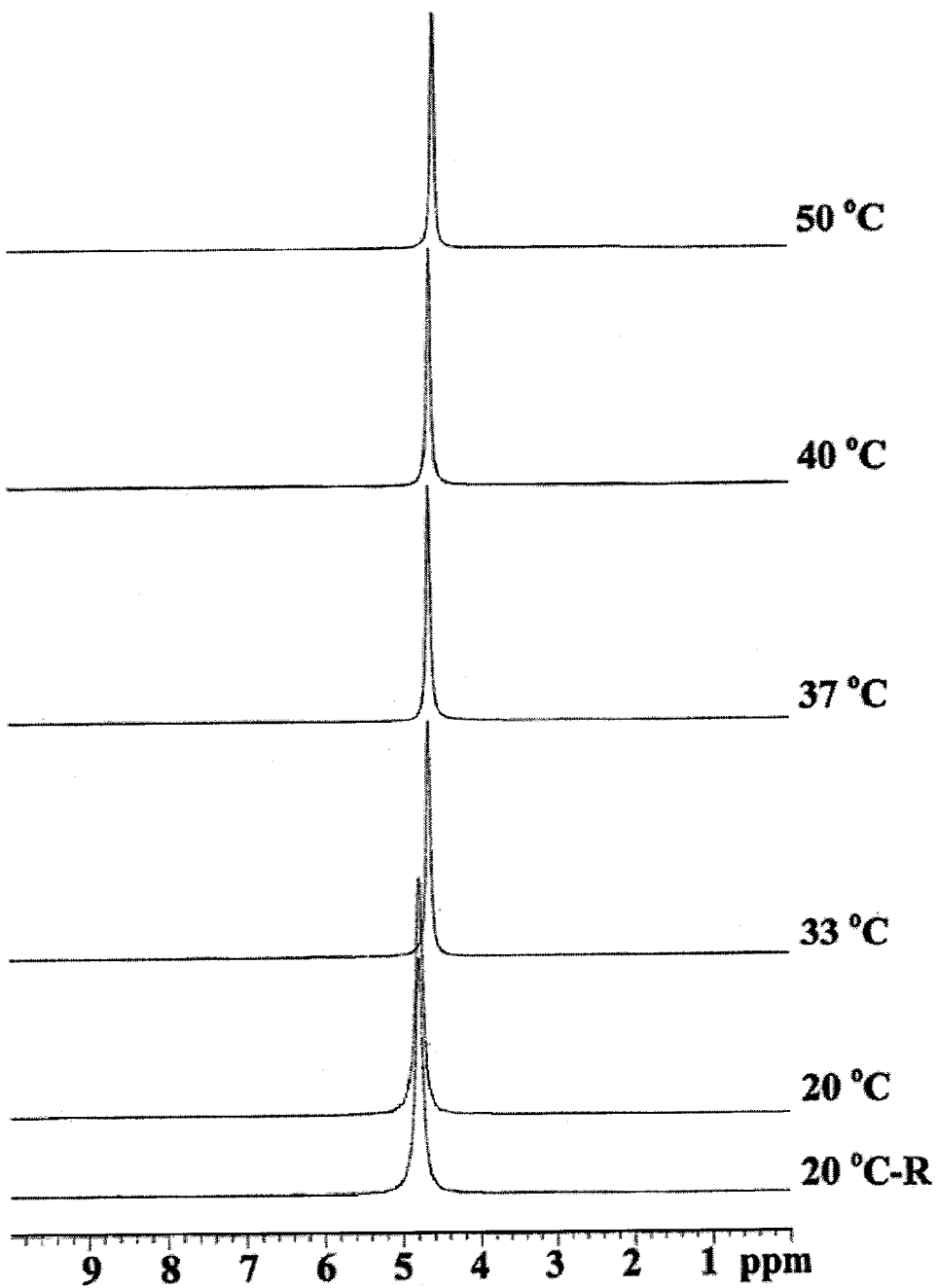
FIG. 13 is a graphical representation of a deuterium NMR showing reversibility of the sol-gel transition.

The reversibility of the sol-gel transition is also confirmed by deuterium NMR (FIG. 13). The peak at 4.8 ppm at 20° C. (sol state) shifted to 4.6 ppm at 33° C. (just above sol-to-gel transition), 4.58 ppm at 37° C. (gel state), 4.56 ppm at 40° C., and 4.5 ppm at 50° C. (syneresis). The change in chemical shift was the most pronounced during the sol-to-gel transition (δ=0.2 ppm) and then during syneresis. When the system is cooled to 20° C., the deuterium peak reappears at 4.8 ppm, indicating the reversibility of the transition. In a sol state, water moves more freely than in a gel state. During the sol-to-gel transition, PEG becomes more hydrophobic due to dehydration and the extent of hydrogen bonding between water molecules and polymers changes. Therefore, the time average environment around deuterium nuclei will be affected, leading to the changes in chemical shift of water during sol-to-gel transition. This finding suggests that the deuterium NMR can be a good method for the determination of sol-gel transition.

The sol-to-gel transition temperature could be controlled from 20° to 40° C. by changing PEG length and composition. When the PEG molecular weight of PLGA-g-PEG increases from 600 to 1000 the sol-to-gel transition occurred at 40° C., whereas the sol-to-gel transition occurred at 20° C. when the PEG composition is decreased by 20% in mole.

Varying Gel Durability:

The time frame for gel durability can be varied by adjusting the ratio of the two blocks in the formula $A_n(B)$ (where n is >2). To test and exemplify the duration of a gel 0.5 g of a polymer solution (see table below) was injected into a 4 ml vial (inner diameter 1.1 cm) and maintaining at 37° C. for 5 minutes to allow the gel to form. After the gel is formed, 3 ml of phosphate buffer saline (37° C., pH=7.4) is added and the vial is placed in a shaker bath (16 strokes/minute). The polymer was monitored daily for complete degradation and the top layer of the buffer was replaced at the time of monitoring. The following table shows the resulting gel durations for each ration of the polymer. PEG-g-PLGA had a molecular weight of 11,000 and PLGA-g-PEG had a molecule weight of 7,800.

| Ratio (PEG-g-PLGA/PLGA-g-PEG) | 100/0 | 60/40 | 50/50 | 40/60 | 0/100 |
|---|---|---|---|---|---|
| Duration of a gel measured as described above. | 1 day~1 week | 3 days~2 weeks | 2~4 weeks | 3~6 weeks | 6~10 weeks |

Conclusions

The aqueous solutions of PEG-g-PLGA copolymers exhibited sol-to-gel transition in response to an increase in temperature. Micelle formation was confirmed by Cryo-TEM and dye solubilization method. The micellar diameter was about 9 nm and CMC was in a range of 0.01–0.05 wt.

%. $^{13}$C-NMR shows that the molecular motion of PEG backbones decreases while that of PLGA side chains increases during sol-to-gel transition. [0001] The 21–25 wt. % solutions exhibit low viscosity at room temperature and form gels at body temperature. The gel morphology changed from turbid to transparent, and the integrity of gel persisted for one week suggesting a promising candidate for short-term drug delivery systems.

The aqueous PLGA-g-PEG system showing a reversible sol-to-gel transition by increasing temperature was studied by dynamic mechanical analysis and NMR spectrophotometer. The rheological study of the copolymers in aqueous solution demonstrated that thermogelation occurred at about 30° C. and the elastic gel modulus exhibited a maximum around body temperature (37° C.). A preliminary in vivo study in a rat model confirmed in situ gel formation after subcutaneous injection of a 0.5 ml aqueous solution. The gel was still present at the injection site after 2 months. This fact clearly distinguishes this polymer from poly(ethylene glycol)-g-poly(DL-lactic acid-co-glycolic acid) PEG-g-PLGA copolymer hydrogels, which disintegrated in one week.

The systems developed in this study are very promising for local delivery of bioactive agents such as proteins, anticancer drugs, and antiathritis drugs by subcutaneous, intraperitoneal, ocular, vaginal or rectal administrations. Thermosensitivity enables the in-situ gel formation upon injection, therefore no surgical procedure is required to implant the drug delivery system and no organic solvent is needed for drug formulation. The physical properties of soft hydrogels reduce mechanical tissue irritation surrounding the injection site. Also, the polymers are biodegradable; therefore there is no need for surgical removal of the implant after the release of the pharmaceutical agent.

Polypeptide Polymer Systems

Another embodiment of the polymer drug-delivery systems comprises polypeptide polymer drug-delivery systems. The polypeptide drug-delivery systems ("polypeptide delivery system") comprise, in part, enzymatically degradable polypeptides. The PEG/PLGA polymer systems disclosed above may generate lactic acid and glycolic acid, during degradation. Such degradation byproducts may result in the degradation of acid sensitive drugs, denaturation of protein drugs, and may influence cell viability during cell delivery. Further, due to vulnerability of PLGA to hydrolysis, PEG/PLGA polymer systems are preferably stored at refrigerator or freezer temperatures. In addition, the relatively low glass transition temperature of PEG/PLGA polymer systems cause it to be a thick paste which can be difficult to handle.

To overcome the disadvantages of certain polymers of the PEG/PLGA polymer systems, enzymatically degradable polypeptide delivery systems are also disclosed herein. The peptide bonds in the polypeptide delivery systems are more stable against hydrolysis than are the ester bonds in PEG/PLGA polymer systems, thereby providing superior storage stability. Thus, the polypeptide delivery systems may be stored as water solutions, requiring no reconstitution.

The degradation products of the polypeptide delivery systems are neutral amino acids. Consequently, there is no significant pH drop during degradation of the polymer, and acid-sensitive proteins/cells are protected. The polypeptide delivery systems are, thus, ideal for delivering acid sensitive bioactive agents.

The polypeptide delivery systems disclosed herein have higher glass transition temperatures than do the esters of the PEG/PLGA polymer systems. Accordingly, the polypeptide delivery systems may be provided in a powder form rather than the paste-form encountered with certain PEG/PLGA systems. A powder form may be more convenient to handle for weighing, reconstitution, and processing. The polypeptide delivery systems may be especially efficient as in-situ, thermogelling depot systems for delivery of proteins, cells, and other such acid-sensitive systems.

As set forth above in relation to the other new, thermogelling, biodegradable polymer systems, the polypeptide delivery systems may include one or more effective biodegradable, bioactive agents. A drug delivery system may comprise, for example, an effective amount of bioactive agent contained in a thermal gelling biodegradable aqueous polypeptide polymer solution. The polypeptide polymer solution may comprise a biodegradable polypeptide block linked to a second polymer block, as set forth below. The bioactive agent may be the same as or similar to those set forth above in relation to the PEG/PLGA polymer systems. Likewise, the polypeptide delivery systems disclosed herein should satisfy all of the drug delivery parameters, characteristics, advantages, and functions set forth above in relation to the PEG/PLGA polymer systems.

More specifically, the polypeptide delivery systems may comprise a biodegradable polymer having a biodegradable polypeptide block linked to a second polymer block to form a graft or linear polymer. The polypeptide delivery system satisfies a general structure comprising the formula of $C_nD_m$, wherein n is equal to or greater than 1, m is equal to or greater than 1, C is a biodegradable polypeptide block, and D may comprise a biocompatible, soluble polymer having a length such that if D is not biodegradable, D may be eliminated by the kidney through the glomeruli filtration system. When D comprises a biodegradable polymer, the length of D is not so limited. For example, D may comprise the same polypeptide block polymer as C, a different polypeptide block polymer or a non-polypeptide polymer, such as PEG. D may comprise any structure that would allow modification to accommodate active groups such that the polypeptide block may be coupled thereto.

The thermogelling, biodegradable, aqueous polymers, when prepared according to the formula $C_nD_m$ work well with n and/or m between 1 and 20. The polypeptide block preferably has an average molecular weight of from about 300 to about 30,000, and more preferably from about 500 to about 10,000.

Polypeptides suitable for the polypeptide delivery systems preferably comprise two or more amino acids wherein at least one of the amino acids is hydrophilic or hydrophobic as compared to the other amino acid(s) of the polypeptide. That is, there is a hydrophilic/hydrophobic relationship between the amino acids of the polypeptide. The polypeptide constituents may comprise alanine (A), isoleucine (I), phenylalanine (F), threonine (T), arginine (R), asparagine (N), aspartic acid (D), cysteine (C), glutamine (Q), glutamic acid (E), glycine (G), histidine (H), leucine (L), lysine (K), methionine (M), proline (P), serine (S), tryptophan (W), tyrosine (Y) or valine (V). The resulting polypeptide may comprise any combination of the listed constituents having a hydrophilic/hydrophobic relationship there between.

For example, the polypeptide drug-delivery system may comprise a polypeptide/polyethylene glycol copolymer. In an embodiment of a polypeptide-polyethylene glycol (PP/PEG) copolymer system, the polypeptide block preferably has an average molecular weight of from about 300 to about 30,000, and more preferably from about 500 to about 10,000. It is preferred that the polyethylene glycol (PEG) block have an average molecular weight of between about 300 and 20,000 and is more preferably between about 500 and 10,000. The PEG block with a higher molecular weight than 10,000 may be difficult to filter through glomeruli filtration.

Having described the polypeptide drug-delivery polymers of the invention, the following experimental examples are given. These specific examples are not intended to limit the scope of the invention described in this application.

Synthesis of Polypeptide/Polyethylene Glycol Polymers

Materials:

Methoxy terminated polyethylene glycol (m.w. from about 300 to about 30,000; Aldrich), polyethylene glycol (m.w. 1000; Aldrich), hexamethylene diisocyanate (HMDI), N-carboxy anhydride-Isoleucine (NCA-Isoleucine), NCA-phenylalanine may be synthesized using standard methods as known to those persons skilled in the art.

General Synthesis:

N-carboxy anhydride (NCA) of alpha-amino acid, such as alanine (A), isoleucine (I), phenylalanine (F), threonine (T) are synthesized by reacting alpha amino acids and phosgene.

Triblock copolymers, polypeptide-b-poly(ethylene glycol)-b-polypeptide (PP-PEG-PP) are synthesized by combining polyethylene glycol with one or two kinds of NCA-alpha amino acids in toluene at a temperature of from about 20 to 120° C. A specific example is set forth below as illustration.

Poly(ethylene glycol)-b-polypeptide-b-poly(ethylene glycol) (PEG-PP-PEG) may be synthesized by combining methoxy terminated PEG with NCA-alpha amino acid to make a di-block copolymer of PEG-PP. The di-block copolymers are coupled using coupling agents such as hexamethylene diisocyanate (HMDI). A specific example is set forth below for illustration.

Synthesis of polyisoleucine-b-poly(ethylene glycol)-b-polyisoleucine (PI-PEG-PI):

About 0.5 to about 2 grams of NCA-isoleucine and about 1 gram PEG (m.w. about 1000) are mixed and reacted at about 60° C. for about 24 hours. Ethyl ether is added to the reaction mixture to precipitate out the resulting polyisoleucine-b-poly(ethylene glycol)-b-polyisoleucine (PI-PEG-PI). The product is placed under high vacuum (about $10^{-3}$ mm Hg) for about 48 hours to remove any residual solvent.

The sol-to-gel transition of the polyisoleucine-b-poly(ethylene glycol)-b-polyisoleucine (PI-PEG-PI) may be measured utilizing standard methods, such as the inverted test tube method or falling ball method, and is expected to be in the range of from about 0 to about 40° C. The molecular weight of the resulting polyisoleucine-b-poly(ethylene glycol)-b-polyisoleucine is expected to be from about 1500 to about 20,000.

Synthesis of poly(isoleucine-co-phenylalanine)-b-poly(ethylene glycol)-b-poly(isoleucine-co-phenylalanine) (PIF-PEG-PIF):

About 0.5 to about 1 gram of NCA-Isoleucine, from about 0.1 to about 1 g of NCA-phenylalanine, and about 1 gram of PEG (m.w. about 1000) are mixed and reacted at about 60° C. for about 24 hours. Ethyl ether is added to the reaction mixture to precipitate out resulting poly(isoleucine-co-phenyl alanine)-b-poly(ethylene glycol)-b-poly(isoleucine-co-phenylalanine) (PIF-PEG-PIF). The product is placed under high vacuum (about $10^{-3}$ mm Hg) for about 48 hours to remove any residual solvent.

The sol-to-gel transition of the poly(isoleucine-co-phenyl alanine)-b-poly(ethylene glycol)-b-poly(isoleucine-co-phenylalanine) is tested and expected to be in the range of from about 0 to about 40° C. The molecular weight is expected to be about 1500 to about 20,000.

Synthesis of Poly(ethylene glycol)-b-polyisoleucine-b-poly(ethylene glycol) (PEG-PI-PEG):

Poly(ethylene glycol)-b-polyisoleucine-b-poly(ethylene glycol) (PEG-PI-PEG) is synthesized by combining about 1 gram of methoxy terminated PEG (m.w. about 550) with from about 0.5 to about 2 grams NCA-isoleucine in toluene at about 60° C., resulting in a diblock copolymer of PEG-PP. The diblock copolymer of PEG-PP is coupled using hexamethylene diisocyanate (HMDI). Ethyl ether is then used to precipitate out the triblock copolymer, PEG-PI-PEG. The product is placed under high vacuum (about $10^{-3}$ mm Hg) for about 48 hours to remove any residual solvent.

The sol-to-gel transition of the PEG-PI-PEG is expected to be at about 0 to about 40° C. The molecular weight is expected to be from about 1500 to about 20,000.

Synthesis of Poly(ethylene glycol)-b-poly(isoleucine-co-phenyl alanine)-b-poly(ethylene glycol) (PEG-PIF-PEG):

Poly(ethylene glycol)-b-poly(isoleucine-co-phenyl alanine)-b-poly(ethylene glycol) (PEG-PIF-PEG) is synthesized by combining about 1 gram of methoxy terminated PEG (m.w. about 550) with about 0.5 to about 2 grams of NCA-isoleucine and about 0.1 to about 1 gram of NCA-phenylalanine in toluene at about 60° C. to form a diblock copolymer of PEG-PP. The PEG-PP diblock copolymer is coupled by using hexamethylene diisocyanate (HMDI). Ethyl ether is used to precipitate out the resulting triblock copolymer PEG-PIF-PEG.

The sol-to-gel transition of the resulting PEG-PIF-PEG is expected to be from about 0 to about 40° C. The molecular weight is expected to be from about 1500 to about 20,000.

Graft copolymers or other topologies having graft numbers greater than 2 are synthesized in similar manners, as would be readily achieved by those skilled in the art having reviewed this disclosure.

While the invention has been illustrated using certain specific embodiments thereof, it will be understood that it is capable of further modifications and this application covers any variations, uses, or adaptations of the invention following, in general, the principles of the invention and including such departures from the present disclosure as come within known or customary practice within the art to which the invention pertains and as may be applied to the essential features herein and as follows in scope of the appended claims.

The invention claimed is:

1. A thermogelling, biodegradable polymer comprising:
   i. a biocompatible polymer block; and
   ii. a polypeptide block,
   iii. wherein the biocompatible polymer and the polypeptide blocks are linked to form a copolymer that undergoes a solution-to-gel transition in response to an increase in temperature from a temperature below the gelling temperature of the copolymer to about body temperature and has a general structure satisfying the formula $C_n D_m$, wherein n is equal to or greater than 1, m is equal to or greater than 1, C is a biodegradable polypeptide block, D is a biocompatible soluble polymer having a chain length such that if D is not biodegradable, D may be eliminated through a glomeruli filtration system, and C is different from D.

2. The thermogelling, biodegradable polymer of claim 1, wherein the polymer is in a powder form.

3. The thermogelling, biodegradable polymer of claim 1, wherein D comprises a biodegradable polymer.

4. The thermogelling, biodegradable polymer of claim 1, wherein C comprises an enzymatically biodegradable polypeptide and D comprises a biodegradable polymer.

5. The thermogelling, biodegradable polymer of claim 1, wherein C is a polypeptide block comprising at least two amino acids, wherein at least one of the amino acids is hydrophilic relative to the other amino acid of the polypeptide block.

6. The thermogelling, biodegradable polymer of claim 1, wherein D comprises a polyethylene glycol block.

7. The thermogelling, biodegradable polymer of claim 1, wherein n is between 1 and 20.

8. The thermogelling, biodegradable polymer of claim 1, wherein n and m are each between 1 and 20.

9. The thermogelling, biodegradable polymer of claim 6, wherein the polyethylene glycol has a weight average molecular weight of from about 300 to about 20,000.

10. The thermogelling, biodegradable polymer of claim 6, wherein the polyethylene glycol block has a weight average molecular weight of from about 500 to about 10,000.

11. The thermogelling, biodegradable polymer of claim 1, wherein the polypeptide block has a weight average molecular weight of from about 300 to about 30,000.

12. The thermogelling, biodegradable polymer of claim 1, wherein the polypeptide block has a weight average molecular weight of from about 500 to about 10,000.

13. The thermogelling, biodegradable polymer of claim 1, wherein the thermogelling, biodegradable polymer does not raise a pH value of a surrounding solution as the polymer biodegrades.

14. The thermogelling, biocompatible polymer of claim 1, further comprising a bioactive agent.

15. A biocompatible, bioactive agent delivery system, comprising:
   an effective amount of bioactive agent contained in a thermogelling, aqueous polymer solution, the polymer solution comprising,
   i. a biocompatible polymer block;
   ii. a biodegradable polypeptide block, wherein the biocompatible polymer and the polypeptide blocks are linked to form a polymer that undergoes a solution-to-gel transition in response to an increase in temperature from a temperature below the gelling temperature of the polymer to about 37° C. and has a general structure satisfying the formula $C_nD_m$, wherein n is equal to or greater than 1, m is equal to or greater than 1, C is a biodegradable polypeptide block, D is a biocompatible soluble polymer having a chain length such that if D is not biodegradable, D may be eliminated through a glomeruli filtration system; and
   iii. an aqueous solvent.

16. The biocompatible, bioactive agent delivery system of claim 15, wherein the bioactive agent is a drug.

17. The biocompatible, bioactive agent delivery system of claim 15, wherein the bioactive agent is selected from the group consisting essentially of anti-cancer agents, hormones, antibiotics, narcotic antagonists, analgesics, anti-inflammatory agents, anti-depressants, anti-epileptics, anti-malarial agents, immunoactivators, growth factors, radioprotection agents, vaccines, gene therapy agents, oligonucleotides, antisense, peptides, proteins, cells, and combinations thereof.

18. The biocompatible, bioactive agent delivery system of claim 16, wherein the drug is selected from the group consisting of oxytocin, vasopressin, adrenocorticotropic growth factor (PDGF), prolactin, luliberin or luteinising hormone releasing hormone (LHRH), growth hormone, growth hormone releasing factor, insulin, somatostatin, glucagons, interleukin-2 (IL-2), interferon-$\alpha,\beta,\gamma$ (IFN-$\alpha,\beta,\gamma$), gastrin, tetragastrin, pentagastrin, urogastroine, secretin, calcitonin, enkephalins, endorphins, angiotensins, thyrotropin releasing hormone (TRH), tumor necrosis factor (TNF), nerve growth factor (NGF), granulocyte-colony stimulating factor (G-CSF), granulocyte macrophage-colony stimulating factor (M-CSF), rennin, bradykinin, bacitracins, alpha-1 antitrypsin, platelet derived growth factor, albumin, antithrombin III, glucocerebrosidase, DNAse, tissue plasminogen activator, clotting factors VII, VIII, and IX, LHRH antagonists, insulin, erythropoietin, polymixins, colistins, tyrocidin, gramicidines, and synthetic analogues, modifications and pharmacologically active fragments thereof, monoclonal antibodies and soluble vaccines.

19. The biocompatible, bioactive agent delivery system of claim 15, wherein the bioactive agent is a cell.

20. The biocompatible, bioactive agent delivery system of claim 15, wherein the thermogelling, biodegradable aqueous polymer does not raise a pH value of a surrounding solution as the polymer biodegrades.

21. A thermogelling, biodegradable polymer drug delivery system comprising:
   i. a biocompatible polymer block;
   ii. a polypeptide block,
   iii. wherein the biocompatible polymer and the polypeptide blocks are linked to form a polymer that undergoes a solution-to-gel transition in response to an increase in temperature from about room temperature to about body temperature and has a general structure satisfying the formula $C_nD_m$, wherein n is equal to or greater than 1, m is equal to or greater than 1, D is a biocompatible soluble polymer having a chain length such that if D is not biodegradable, D may be eliminated through a glomeruli filtration system, and C is a biodegradable polypeptide block comprising at least two amino acids, wherein at least one of the amino acids is hydrophilic relative to the other amino acid; and
   iv. an effective amount of a bioactive agent.

22. The thermogelling, biodegradable polymer of claim 21, wherein D comprises a polyethylene glycol block.

23. The thermogelling, biodegradable polymer of claim 22, wherein the polyethylene glycol block has a weight average molecular weight of from about 300 to about 20,000.

24. The thermogelling, biodegradable polymer of claim 21, wherein D is different from C.

25. The thermogelling, biodegradable polymer of claim 21, wherein C is enzymatically biodegradable.

* * * * *